(12) United States Patent
Uffenheimer et al.

(10) Patent No.: US 7,939,017 B2
(45) Date of Patent: May 10, 2011

(54) AUTOMATED FLUID HANDLING SYSTEM AND METHOD

(76) Inventors: Kenneth F. Uffenheimer, Los Gatos, CA (US); Arthur Hunt, Los Gatos, CA (US)

( * ) Notice: Subject to any disclaimer, the term of this patent is extended or adjusted under 35 U.S.C. 154(b) by 949 days.

(21) Appl. No.: 11/679,289

(22) Filed: Feb. 27, 2007

(65) Prior Publication Data

US 2007/0202608 A1  Aug. 30, 2007

Related U.S. Application Data

(63) Continuation of application No. 10/172,546, filed on Jun. 13, 2002, now Pat. No. 7,198,956.

(60) Provisional application No. 60/298,458, filed on Jun. 13, 2001.

(51) Int. Cl.
  *G01N 21/00* (2006.01)
  *G01N 1/14* (2006.01)
(52) U.S. Cl. ........... 422/63; 422/67; 422/68.1; 422/501; 422/509; 436/180; 436/43
(58) Field of Classification Search .................. 422/100, 422/103, 62–63, 67, 68.1, 501, 509, 537, 422/539; 436/43, 180
See application file for complete search history.

(56) References Cited

U.S. PATENT DOCUMENTS

| | | | |
|---|---|---|---|
| 4,242,909 A | 1/1981 | Gundelfinger | |
| 4,366,119 A * | 12/1982 | Takeuchi | 422/65 |
| 4,501,161 A | 2/1985 | Endo et al. | |
| 4,622,457 A | 11/1986 | Bradley et al. | |
| 4,680,270 A * | 7/1987 | Mitsumaki et al. | 205/778 |
| 4,713,974 A | 12/1987 | Stone | |
| 4,799,393 A | 1/1989 | Uffenheimer | |
| 4,816,730 A | 3/1989 | Wilhelm, Jr. et al. | |
| 4,944,781 A | 7/1990 | Ruggirello et al. | |
| 4,968,485 A | 11/1990 | Morita | |
| 4,979,093 A | 12/1990 | Laine et al. | |
| 5,005,434 A | 4/1991 | Watanabe et al. | |
| 5,012,845 A | 5/1991 | Averette | |
| 5,104,808 A * | 4/1992 | Laska et al. | 436/48 |
| 5,132,088 A | 7/1992 | Wakatake | |
| 5,158,748 A | 10/1992 | Obi et al. | |
| 5,223,434 A | 6/1993 | Kanno et al. | |
| 5,229,074 A | 7/1993 | Heath et al. | |
| 5,268,147 A | 12/1993 | Zabetakis et al. | |
| 5,277,871 A | 1/1994 | Fujii et al. | |
| 5,439,645 A | 8/1995 | Saralegui et al. | |
| 5,441,700 A | 8/1995 | Markelov | |

(Continued)

FOREIGN PATENT DOCUMENTS

EP  0 253 519  1/1988

(Continued)

OTHER PUBLICATIONS

Cytomation Inc., Product Description, "Automation with MoSkeeto AutoSampler, the MoFlo Modular."

(Continued)

*Primary Examiner* — Brian R Gordon
(74) *Attorney, Agent, or Firm* — Kilpatrick Townsend & Stockton LLP

(57) ABSTRACT

An automated fluid handling system configured to prepare fluid samples and to introduce them into an analytical instrument, such as a particle analyzer, flow cytometer or sorter flow cell, and that is capable of analyzing both accurately and quickly.

14 Claims, 18 Drawing Sheets

U.S. PATENT DOCUMENTS

| | | | |
|---|---|---|---|
| 5,468,643 A | 11/1995 | Su et al. | |
| 5,474,744 A | 12/1995 | Lerch | |
| 5,488,469 A | 1/1996 | Yamamoto et al. | |
| 5,545,252 A | 8/1996 | Hinshaw et al. | |
| 5,558,838 A | 9/1996 | Uffenheimer | |
| 5,593,893 A | 1/1997 | Kobashi et al. | |
| 5,639,425 A * | 6/1997 | Komiyama et al. | 422/63 |
| 5,686,656 A | 11/1997 | Amirav et al. | |
| 5,744,099 A | 4/1998 | Chase et al. | |
| 5,756,905 A | 5/1998 | Ueda | |
| 5,783,450 A | 7/1998 | Yoshida et al. | |
| 5,792,423 A | 8/1998 | Markelov | |
| 5,814,277 A | 9/1998 | Bell et al. | |
| 5,814,742 A | 9/1998 | Vissers | |
| 5,820,824 A | 10/1998 | Tanaka | |
| 5,895,764 A | 4/1999 | Sklar et al. | |
| 5,939,326 A | 8/1999 | Chupp et al. | |
| 5,948,360 A | 9/1999 | Rao et al. | |
| 5,998,217 A | 12/1999 | Rao et al. | |
| 6,040,186 A | 3/2000 | Lewis et al. | |
| 6,060,320 A | 5/2000 | Dorenkott et al. | |
| 6,114,122 A | 9/2000 | Besemer et al. | |
| 6,143,573 A | 11/2000 | Rao et al. | |
| 6,190,614 B1 | 2/2001 | Fukunaga | |
| 6,241,890 B1 | 6/2001 | Clay et al. | |
| 6,265,226 B1 | 7/2001 | Petro et al. | |
| 6,296,771 B1 | 10/2001 | Miroslav | |
| 6,315,952 B1 | 11/2001 | Sklar et al. | |
| 6,348,354 B1 | 2/2002 | Adolfsen et al. | |
| 6,358,413 B1 | 3/2002 | Maiefski | |
| 6,428,702 B1 | 8/2002 | Berger et al. | |
| 6,475,437 B1 | 11/2002 | Gerstel et al. | |
| 6,537,818 B2 | 3/2003 | Richards et al. | |
| 6,555,360 B1 | 4/2003 | Srienc et al. | |
| 6,613,579 B2 | 9/2003 | Wolcott | |
| 6,627,157 B1 * | 9/2003 | Doktycz et al. | 422/100 |
| 6,641,783 B1 | 11/2003 | Pidgeon et al. | |
| 6,762,061 B1 * | 7/2004 | Borrelli et al. | 436/180 |
| 6,884,626 B1 | 4/2005 | Borrelli et al. | |
| 6,951,632 B2 | 10/2005 | Unger et al. | |
| 6,976,383 B2 * | 12/2005 | Petro et al. | 73/61.55 |
| 7,227,018 B2 * | 6/2007 | Shoji et al. | 536/25.41 |
| 7,267,800 B2 * | 9/2007 | Takii et al. | 422/100 |
| 2001/0004449 A1 | 6/2001 | Suzuki et al. | |
| 2001/0010936 A1 | 8/2001 | Richards et al. | |
| 2001/0026772 A1 | 10/2001 | Fuerst et al. | |
| 2002/0006356 A1 | 1/2002 | Neal et al. | |
| 2002/0006668 A1 | 1/2002 | Takahashi et al. | |
| 2003/0143123 A1 | 7/2003 | Maeda | |
| 2004/0072365 A1 * | 4/2004 | Rose et al. | 436/180 |
| 2004/0166028 A1 | 8/2004 | Husar et al. | |

FOREIGN PATENT DOCUMENTS

| | | |
|---|---|---|
| EP | 0 602 416 B1 | 6/1994 |
| EP | 0 645 631 A2 | 3/1995 |
| EP | 0 645 631 A3 | 3/1995 |
| EP | 670483 | 9/1995 |
| JP | 05-060736 | 3/1993 |
| WO | WO 00/20873 | 4/2000 |
| WO | WO 01/59429 | 8/2001 |
| WO | WO 01/90295 | 11/2001 |
| WO | WO 02/101360 | 12/2002 |

OTHER PUBLICATIONS

Cytomation Inc., Product Description, "Coulter Epics XL/XL-MCL" Brochure Page.

Cytomation Inc., Product Description, "Flow Cytometry—Automated Microsampler System."

Edwards, B., "Plug flow cytometry: An automated coupling device for rapid sequential flow cytometric sample analysis", *Cytometry*, 37: 156-159 (1999).

Edwards, B., et al., "Plug flow cytometry extends analytical capabilities in cell adhesion and receptor pharmacology", *Cytometry*, 43: 211-216 (2001).

* cited by examiner

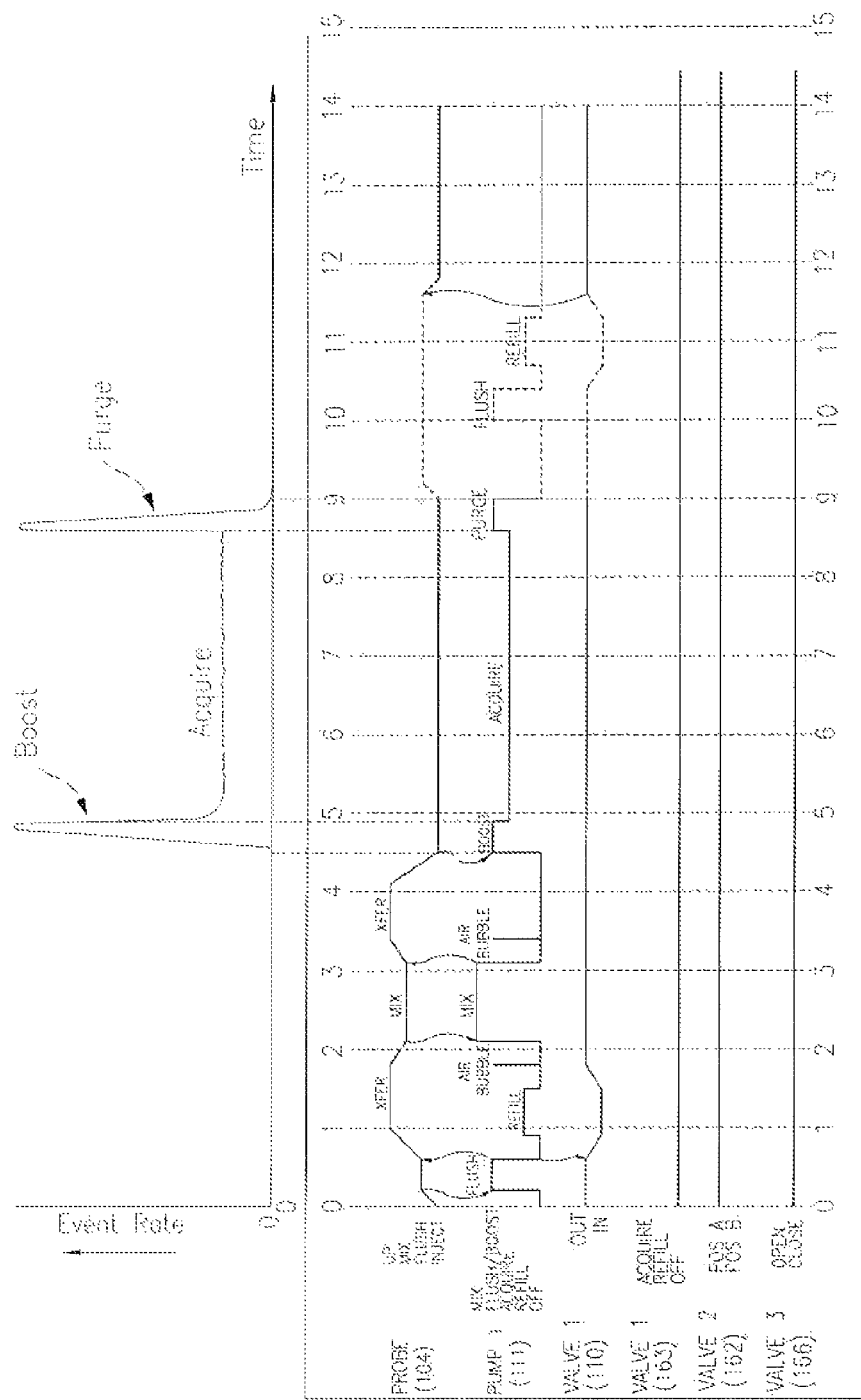
FIG 4A  STANDARD MODE OF OPERATION

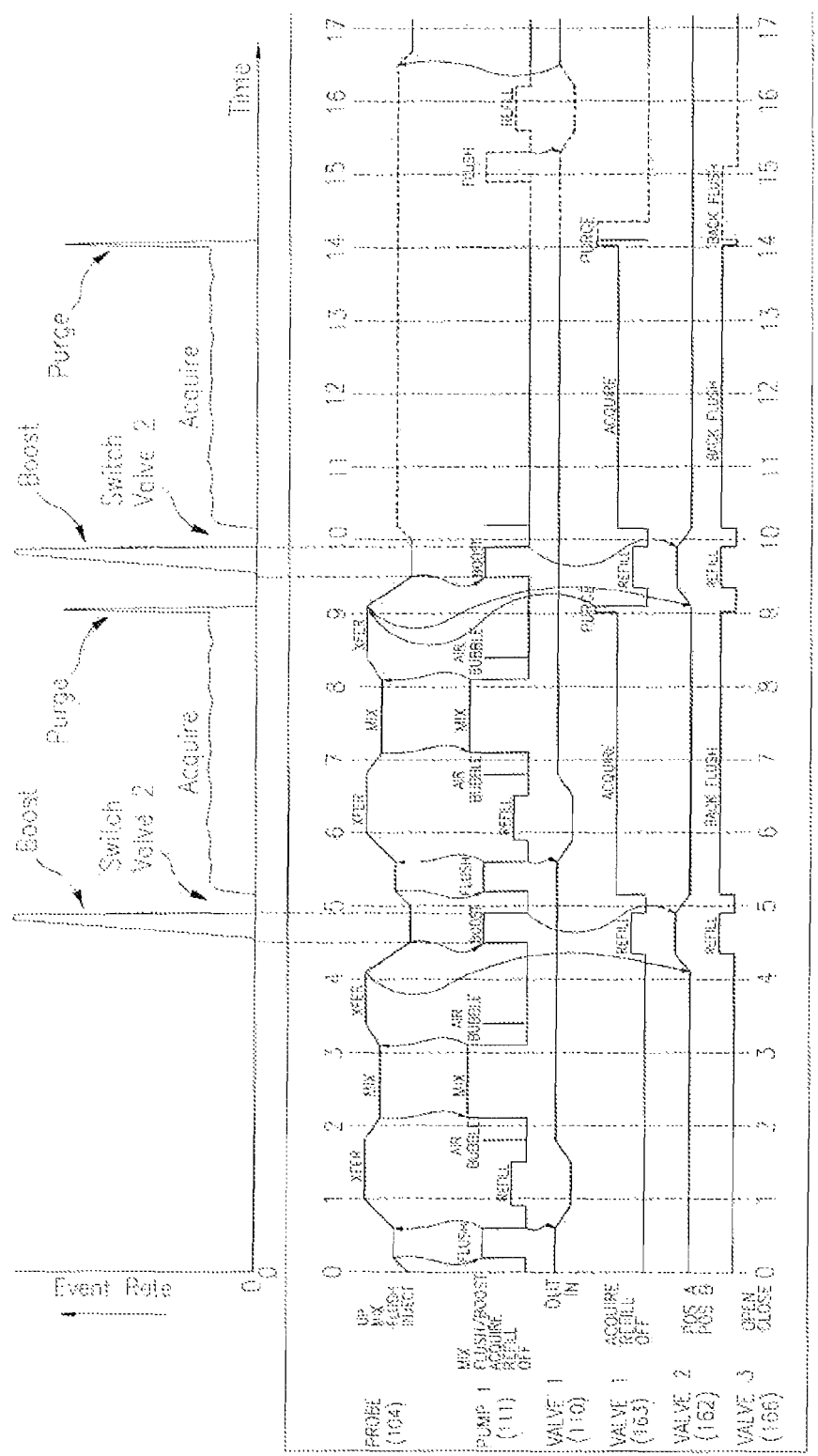

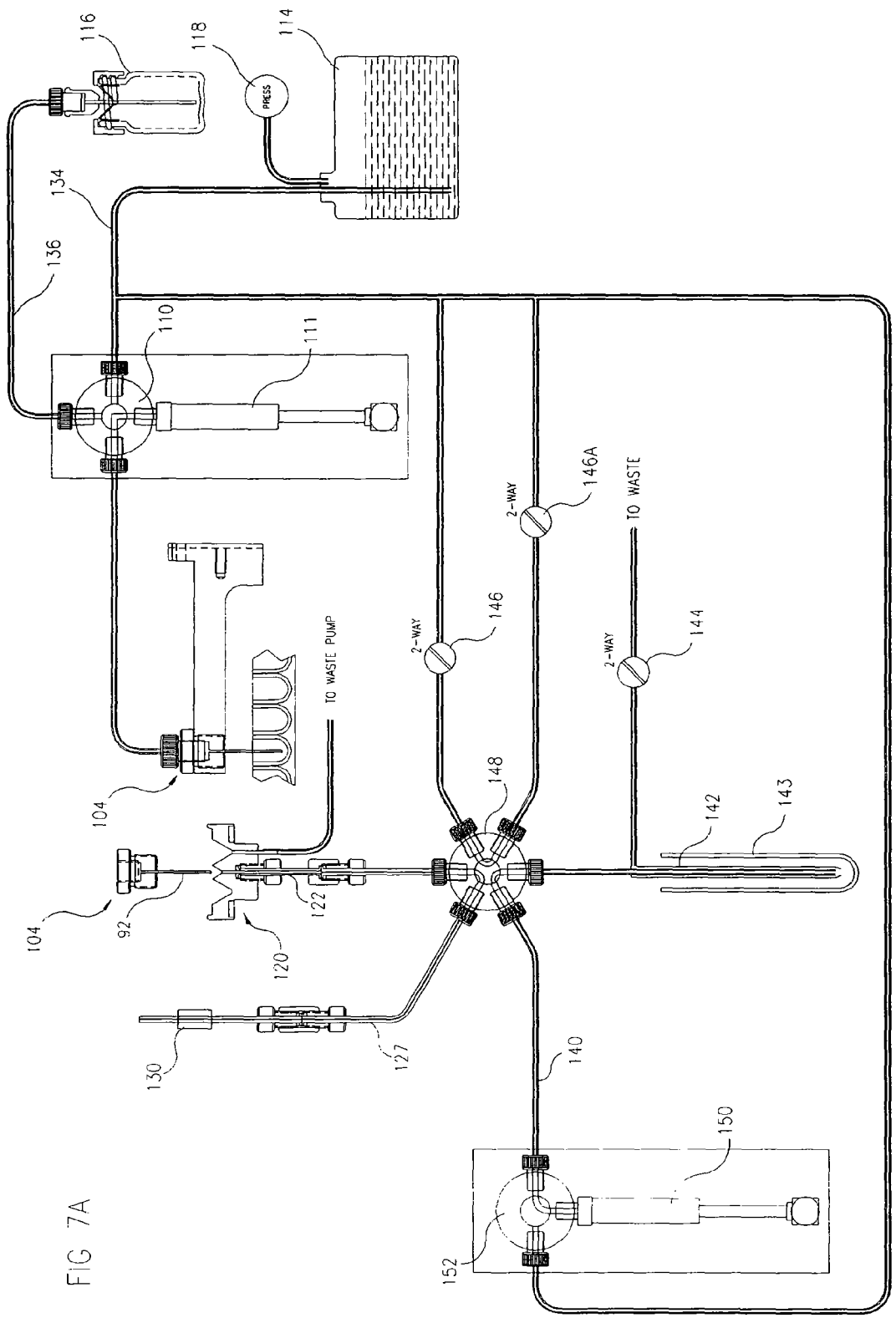

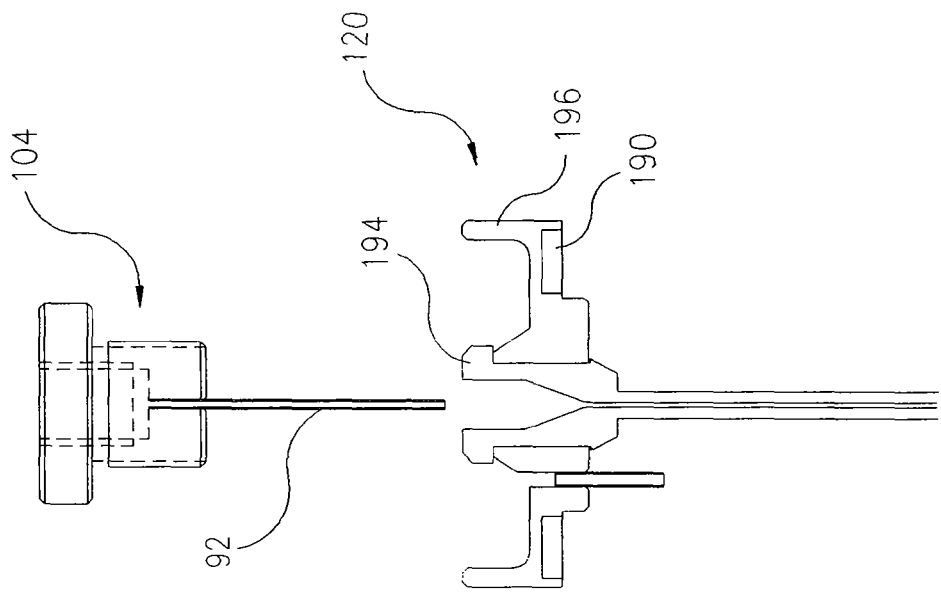
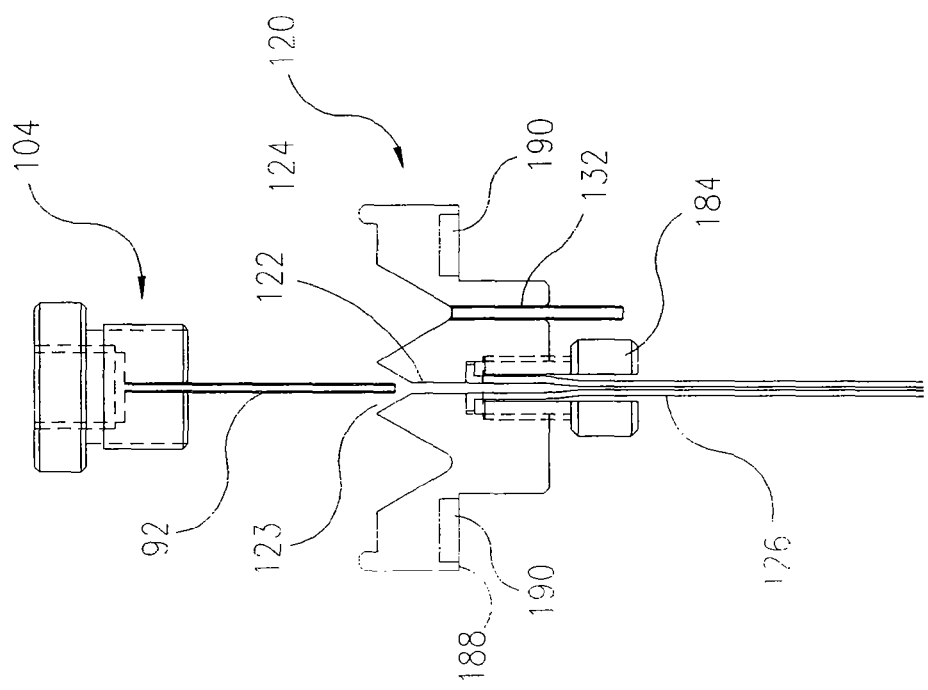
FIG 12
FIG 13

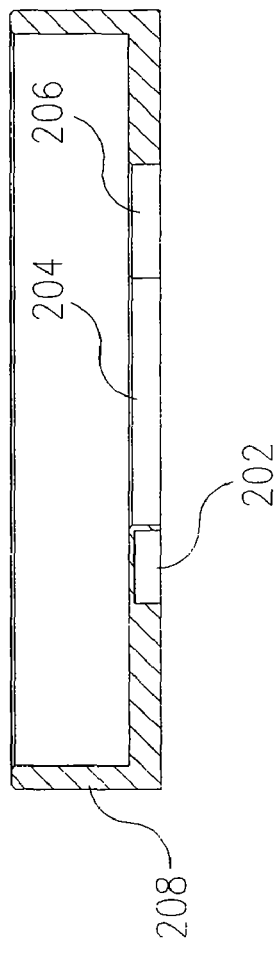
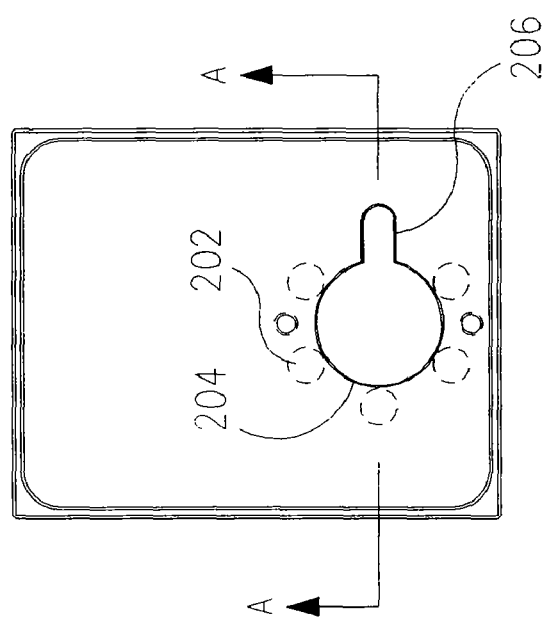

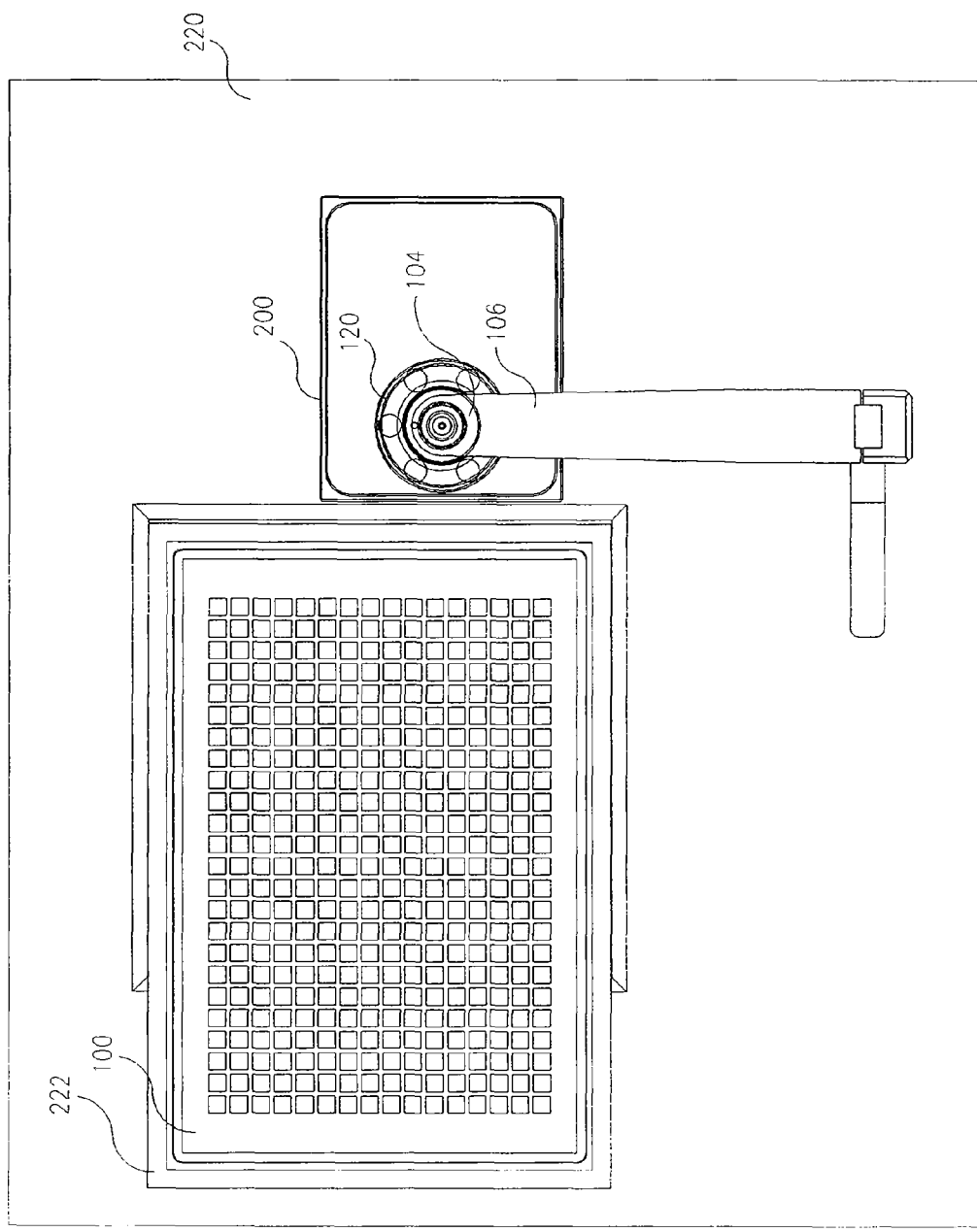

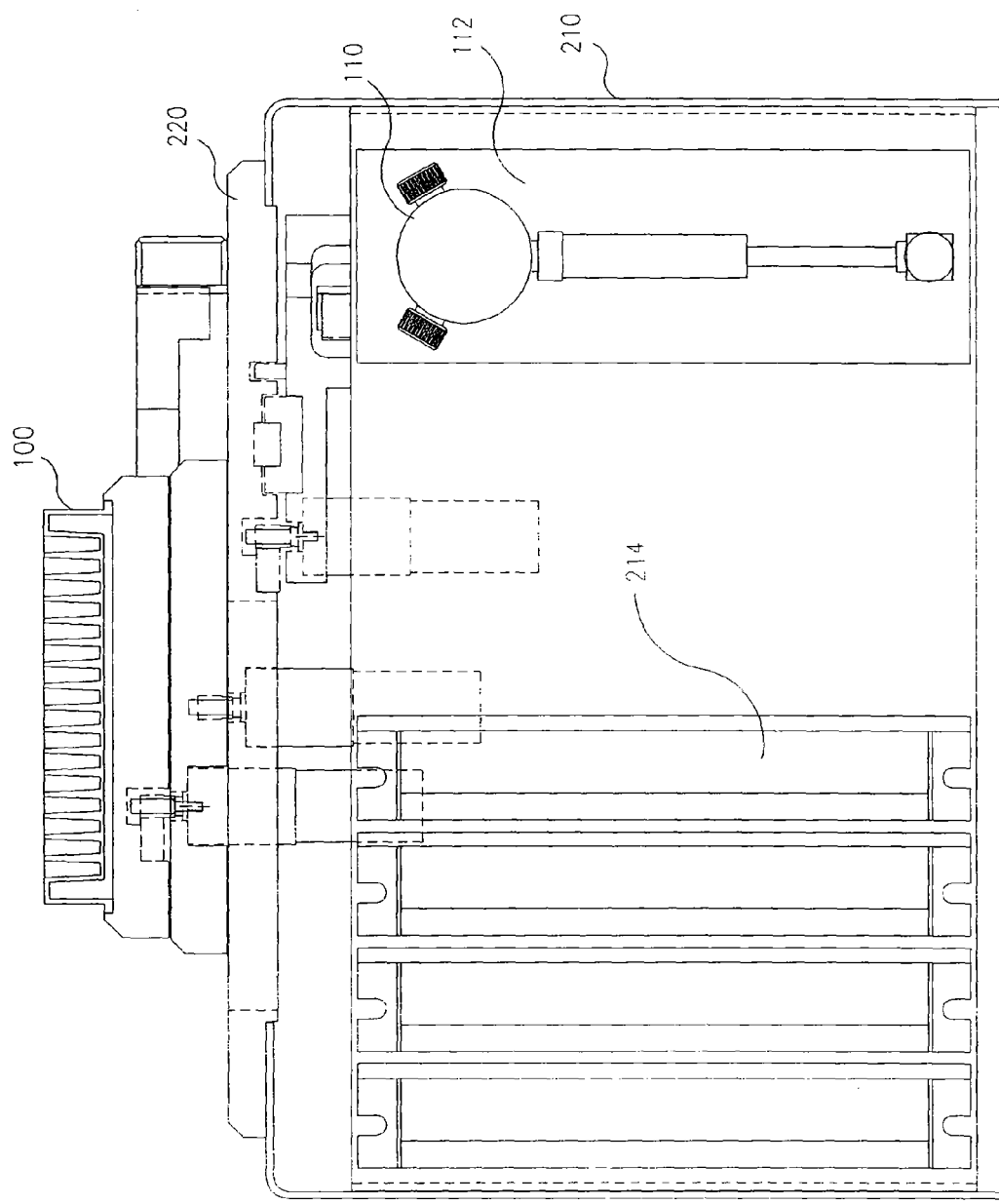

AUTOMATED FLUID HANDLING SYSTEM AND METHOD

CROSS-REFERENCES TO RELATED APPLICATIONS

This application is a continuation of U.S. application Ser. No. 10/172,546, filed on Jun. 13, 2002, which claims the benefit of U.S. Provisional Application No. 60/298,458, filed on Jun. 13, 2001, the full disclosures of which are incorporated herein by reference.

BACKGROUND OF THE INVENTION

1. Field of the Invention

The present invention relates generally to laboratory equipment. More specifically, it relates to an automated fluid handling system configured to prepare fluid samples and to introduce them into an analytical instrument, such as a particle analyzer, flow cytometer or sorter flow cell.

There is a tremendous and growing need for rapid and accurate analysis of biological and chemical samples, both in a hospital/clinical setting and in a laboratory/research setting. Automated preparation and handling of biological and chemical samples can provide an efficient and cost effective answer to this growing need. Many existing devices have been developed to meet this need. However, the prior art has heretofore been characterized by a number of shortcomings.

Many prior art fluid control devices are characterized by an inverse relationship between the speed with which samples are analyzed and the accuracy of the analysis obtained. Such devices are unable to analyze samples both quickly and accurately, and must sacrifice some performance in one to achieve increased performance in the other. For example some preexisting apparatus increase the speed with which samples are analyzed by simply running faster and pushing the sample faster through an analytical instrument, such as a particle analyzer, flow cytometer or cell sorter. However, the fluid may be moving through the analyzer at faster than optimal speeds, which may decrease the accuracy of the analysis obtained.

Many prior devices are limited to sampling a fixed volume. These devices typically are capable of analyzing only relatively small samples and are thus not useable for analyzing rare events, which typically require large sample sizes.

Another problem with many prior devices is a cross contamination level between samples (often called carryover) of 5% and more. Cross contamination between samples reduces the accuracy of sample results.

Other pre-existing systems are useable only with pre-prepared samples, and cannot be used to prepare, mix and analyze samples. This can be a disadvantage where samples must be analyzed very quickly after preparation, and may also increase the cost and expense of analyzing a sample, as additional equipment must be obtained to prepare the sample in advance of using the fluid control device.

Some fluid handling systems pressurize sample wells to force samples into the system. This method is not useable with filter-bottom plates. Still other systems are configured so that they inadvertently dilute samples, or are unable to pump an accurate volume or at an optimal and accurate flow rate.

What is needed is a fluid handling system that overcomes some of the disadvantages of the prior art by providing a system that is (1) capable of analyzing more accurately and more quickly than pre-existing devices; (2) capable of preparing samples prior to introducing the samples to an analyzer; (3) having a selectable volume; (4) capable of minimizing sample carryover to approximately less than 0.05%; (5) capable of utilizing the full volume of sample; (6) capable of providing accurate sample per unit volume without severely reducing throughput; (7) capable of cleansing the sample probe, thus reducing carryover and contamination between samples; (8) and having means for preventing the mixing of sample and fluids en route to an analytical instrument. The present invention is designed to meet these needs.

BRIEF SUMMARY OF THE INVENTION

The invention includes, in one aspect, an automated fluid-handling system for use with an analytical instrument for analyzing samples. The system includes a sample-holding station for holding a plurality of samples to be analyzed, an injection port adapted to be coupled to the analytical instrument, and through which sample material can be supplied to the instrument, and a sample probe that is moveable between each of a selected sample in the station and the injection port, for transferring the selected sample to the injection port. A first pump in the system is connected to the sample probe, and operable to effect the transfer of a selected volume of sample into the probe, and to eject the sample volume through the injection port, at a first flow rate. A second pump in the system is adapted to be operably placed between the injection port and the instrument, and is operable to control the rate of movement of the sample volume through the analytical instrument, at a second flow rate.

For use with a flow cytometer analytical instrument, first pump may be operable to inject a sample into the injection port at a rate effective to move sample material at a relatively high flow rate into the instrument, the second pump, to move sample material through the instrument at a relatively slow rate.

The sample-holding station may comprise a motion-controlled stage for holding a microtiter well plate and for selectively positioning the microtiter well plate with respect to the sample probe, enabling the sample probe to address a selected sample well within the microtiter well plate.

In one embodiment, the injection port has a central conical portion with a central bore for sealingly engaging the sample probe and an annular waste trough surrounding the central conical portion. The injection port further comprises a resilient tube in fluid communication with the central bore of the injection port, the resilient tube having an internal diameter sized to create an interference fit when the sample probe is inserted into the resilient tube. The tube between the sample probe and the first pump may be a chromic acid treated polyolefin tube.

Further the system may include a plurality of magnets affixed to the injection port, and a plurality of opposite polarity magnets affixed to the fluid handling system for attachment and registration of the injection port with respect to the fluid handling system, wherein the injection port is detachable from the fluid handling system by rotating the injection port to disengage the magnets from one another and lifting the injection port from the fluid handling system.

The system may further include an injection port holder including an aperture for accepting a portion of the injection port, this aperture being larger than the portion of said injection port, whereby contact of the sample probe with a surface of the recess horizontally displaces the injection port in a direction allowing the sample probe to enter the central bore of the injection port.

The first and/or second pump may be syringe pumps. The system may further include a first distribution valve interposed between the first pump and the sample probe, for selectively connecting the first pump to the sample probe and at least one source of auxiliary fluid.

The system may further include a second switching valve adapted to be operably placed between the injection port and the analytical instrument. This valve has a first position, where the valve connects the second pump to a source of sheath fluid and connects the injection port to the analytical instrument, and a second position, where the switching valve connects the second pump to the analytical instrument and connects the injection port to the source of sheath fluid. The second valve can be placed in a position to connect either the first pump or the second pump in fluid communication with the analytical instrument.

A programmable motion controller in one embodiment of the system is selectively operable, in a high throughput operating mode, to carry out the following functions:

transfer a first sample volume of a first selected sample into a sample probe, eject the first sample volume through an injection port and into the analytical instrument at a first flow rate with the first pump connected to the sample probe, move the first sample volume through the instrument at a second flow rate with the second pump interposed between the injection port and the instrument, while the first sample volume is moving through the instrument, transfer a second sample volume of a second selected sample into the sample probe, and optionally, repeating the ejecting, moving and transferring steps with the second sample volume and one or more of the plurality of samples.

In a related aspect, the invention includes a method of loading and analyzing each of a plurality of samples in an analytical instrument, by the steps of (i) transferring a first sample volume of a first selected sample into a sample probe, (ii) ejecting the first sample volume through an injection port and into the instrument, at a first flow rate with a first pump connected to the sample probe, (iii) moving the first sample volume through the instrument at a second flow rate with a second pump interposed between the injection port and the instrument, (iv) while the first sample volume is moving through the instrument, transferring a second sample volume of a second selected sample into the sample probe, and (v) optionally, repeating the ejecting, moving and transferring steps with the second sample volume and one or more of the plurality of samples.

The transferring step may involve aspirating sheath fluid into said first pump from a sheath fluid reservoir, activating a distribution valve connected to the first pump such that the first pump communicates with the sample probe, aspirating a small amount of air into the tip of the sample probe with the first pump to form a separator bubble, moving a well plate along axes until the first selected sample is positioned below the sample probe, and subsequently lowering the sample probe into a sampling position with the tip of the probe immersed within the first selected sample, reciprocating the first pump to create a suck/spit mixing action and aspirating a sample aliquot into the sample probe separated from the sheath fluid by the separator bubble, and raising the sample probe out of the first selected sample and moving the sample probe into a sample injecting position with the sample probe sealingly engaging the injection port.

The injecting step may involve boosting the sample at a relatively high flow rate through the injection port and into the analytical instrument.

The moving step may involve moving the sample at a reduced flow rate with the second pump for analyzing the sample with the analytical instrument.

The method may further involve, while the first sample volume is moving through the instrument at the second flow rate, and prior to transferring the second sample volume of the second selected sample into the sample probe, disengaging the sample probe from the injection port, and raising the sample probe into a conical portion of the injection port, expelling sheath fluid through the sample probe with the first pump to wash out the sample residue from the sample probe, and to clean an exterior portion of the sample probe, and receiving overflow of fluid from the conical portion of the injection port in a waste trough surrounding the conical portion of the injection port and conveying the overflow of fluid to waste.

The method may further involve aspirating auxiliary reagent into the first pump from an auxiliary reagent supply container, positioning the sample probe tip above the injection port, and priming the reagent through the pumping system, receiving overflow of reagent in the waste trough and conveying the overflow of reagent to waste, with the first pump, pumping a predetermined aliquot of reagent from the sample probe into one or more of said plurality of samples, and mixing the reagent with the sample by turbulence from the dispensed jet of reagent.

In one embodiment, a separation bubble is aspirated into the tip of the probe, the tip is lowered into a well having a first reagent, a volume of reagent is aspirated into the probe tip, the probe tip is transferred to a second well having a quantity of sample, while preserving the integrity of the bubble, the reagent and sample are mixed, and the mixed contents in the probe tip are transferred to the injection port, for ejection therein.

In another aspect, the invention includes an automated fluid-handling system for use with an analytical instrument for analyzing samples. The system includes a sample-holding station for holding a plurality of samples to be analyzed, an injection port adapted to be operably coupled to the analytical instrument, and through which sample material can be supplied to the analytical instrument, and a sample probe that is moveable between each of a selected sample in the station and the injection port, for transferring the selected sample to the injection port, A pump in the system is operable to effect (i) transfer of a volume of a selected sample into the probe, (ii) transfer of a sample volume from the probe through the injection port and into the instrument, at one flow rate, and (iii) transfer of the sample through the instrument at a second flow rate.

Various features mentioned above for the two-pump system that are also applicable to the one-pump system are contemplated.

In a related aspect, the invention includes a method for loading an analytical instrument having a sample flow tube and a detection zone along the tube for detecting a sample volume. The method includes injecting the sample volume into the sample flow tube at a first relatively rapid flow rate such that at least a portion of the sample passes into the detection zone, and adjusting the rate of movement of the sample volume through said detection zone to a second relatively slow flow rate.

Also disclosed is an injection port for a fluid handling system. The port has a central conical portion with a central bore for sealingly engaging a sample probe of the fluid handling system, and an annular waste trough surrounding the central conical portion.

The port may have a plurality of magnets affixed thereto for interacting with and a plurality of opposite polarity magnets affixed to the fluid handling system for attachment and registration of the injection port with respect to the fluid handling system. The port in this embodiment is detachable from the fluid handling system by rotating the injection port to disengage the magnets from one another and lifting the injection port from the fluid handling system.

The port may include a resilient tube in fluid communication with the central bore of the injection port, the tube having an internal diameter sized to create an interference fit when the sample probe is inserted into the resilient tube.

These and other objects and features of the invention will become more fully apparent when the following detailed description of the invention is read in conjunction with the accompanying drawings.

BRIEF DESCRIPTION OF THE DRAWINGS

FIG. 4A is a timing diagram for the standard throughput fluid handling system of FIG. 1.

FIG. 4B is a timing diagram for the high throughput fluid handling system of FIGS. 2 and 3.

FIG. 7A is a schematic diagram of a high throughput fluid handling system configured similarly to FIG. 7, but further including an additional fluid conduit loop.

FIG. 12 is a cross section of an alternate embodiment of the injection port.

FIG. 13 is a cross section of a second alternate embodiment of the injection port.

FIG. 14 is a top view of the injection port holder of the fluid handling system.

FIG. 15 is a side view of the injection port holder.

FIG. 16 is a cross section of the injection port holder taken along line A-A in FIG. 12.

FIG. 17 is a top view of a preferred embodiment of the fluid handling system of the present invention.

FIG. 18 is an end view of the lower portion of the fluid handling system.

DETAILED DESCRIPTION OF THE INVENTION

There is a tremendous and growing need for rapid and accurate analysis of biological and chemical samples, both in a hospital/clinical setting and in a laboratory/research setting. Automated preparation and handling of biological and chemical samples can provide an efficient and cost effective answer to this growing need. One embodiment of the present invention takes the form of a programmable automated fluid handling system configured to prepare fluid samples and to introduce them into an analytical instrument. The fluid handling system can be configured to interface with a particle analyzer, a flow cytometer and many other analytical instruments.

Figure 1:
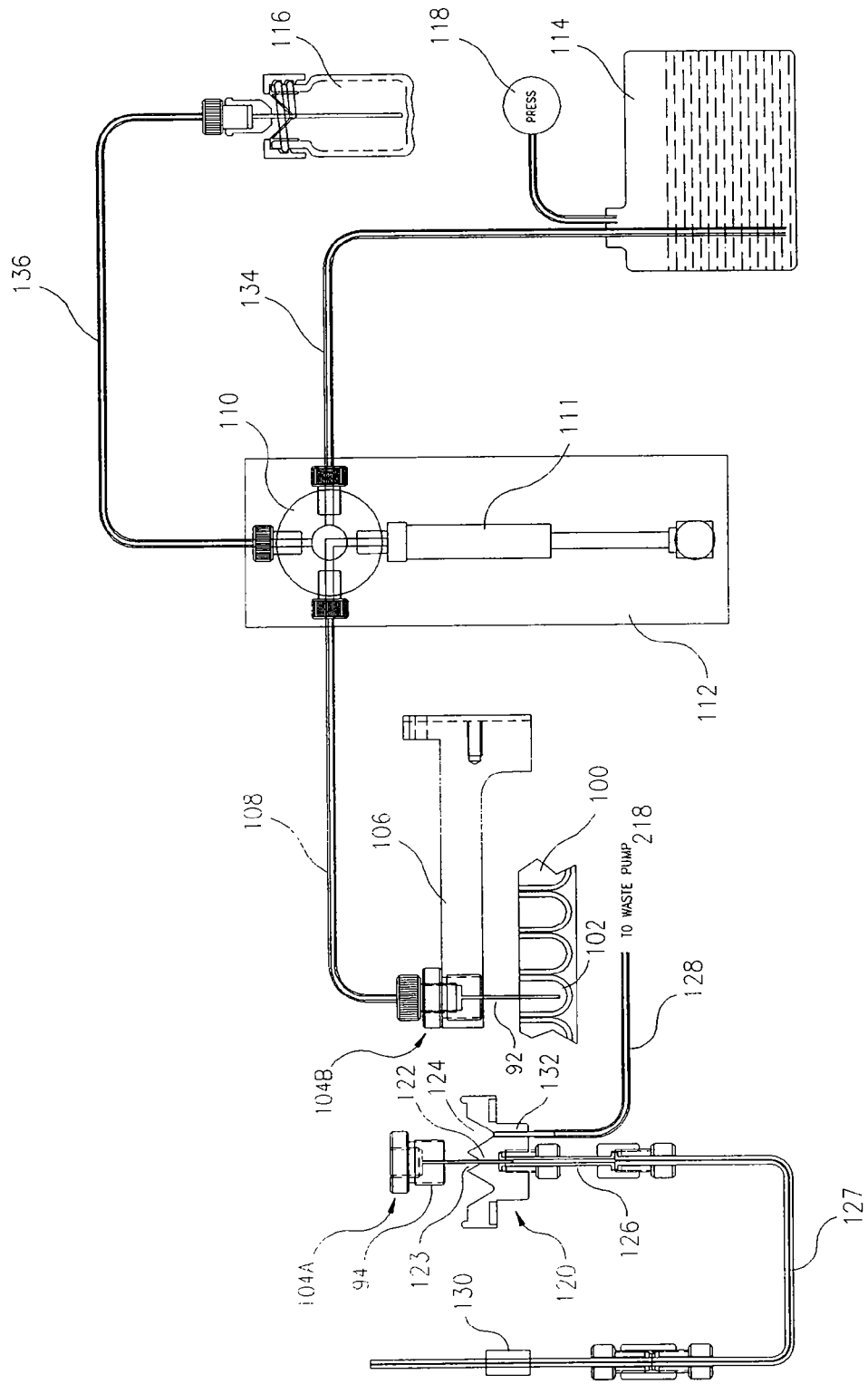
FIG. 1 is a schematic diagram of the fluid circuit of an automated fluid handling system constructed according to the present invention configured for handling samples from a microtiter well plate.

FIG. 1 is a schematic diagram of the fluid circuit of an embodiment of an automated fluid handling system constructed according to the principles of the present invention. The fluid handling system has great versatility and may be assembled in a number of different configurations. The fluid handling system typically comprises a sample-holding station for holding a plurality of samples to be analyzed. In the embodiment shown in FIG. 1, the fluid handling system is configured for handling samples from a microtiter well plate 100. The well plate 100 typically has an array of sample wells 102 arranged in a two dimensional pattern. Common types of well plates include 96 sample wells in a 8.times.12 array or 384 sample wells in a 16.times.24 array. Other types of well plates 100 with other patterns of sample wells 102 may also be used with the fluid handling system, and are well known to those of skill in the art. In one embodiment, the sample-holding station includes a motion-controlled stage for holding a microtiter well plate and for selectively positioning the microtiter well plate with respect to a sample probe to address a selected sample well within the microtiter well plate, as described below.

The fluid handling system includes a sample probe 104, that is moveable between each of a selected sample in the station and an injection port, for transferring the selected sample to the injection port 120. Probe 104A and 104B shown in FIG. 1 are the same probe. Probe 104A illustrates the probe in position to interact with the injection port/wash station 120. The probe marked 104B represents the probe in position to interact with a sample in sample well 102. Because probes 104A and 104B are the same probe, subsequent references to this feature in the text and in the drawings will be identified only by the number 104.

In one embodiment, the sample probe includes a tubular member 92 of sufficient length to reach the bottom of each sample well 102, and a body 94 or other known structure used to hold the tubular member 92. The sample probe 104 may be mounted on the end of a movable probe arm 106. In the embodiment described herein, the probe arm 106 may be moved horizontally between a position A for engaging the injection port/wash station 120, and a position B for engaging the sample wells 102. In this embodiment, the fluid handling system is further constructed so that the sample probe 104 is capable of selectively addressing each individual sample well 102 by moving the probe arm 106 in the vertical axis, and by moving the well plate 100 horizontally along X and Y axes. However, in alternate embodiments, probe arm 106 is movable along three axes, a vertical or Z axis and horizontal X and Y axes, to selectively engage sample wells 102. In other alternate embodiments, the probe arm 106 may be limited to zero, or two axes of movement, and instead the plate 100 may be moved in any axis in which the movement of the probe arm 106 is limited.

When in the sample injecting position, the sample probe 104 sealingly engages the injection tubing 126 connected to the central bore 122 of the injection port/wash station 120. The injection port/wash station 120, which will be described in greater detail below in connection with FIGS. 8-11, has a central bore 122, surrounded by an annular waste trough 124. In one embodiment, the injection port is adapted to be operably coupled to an analytical instrument and through which sample material can be supplied to the instrument. The central bore 122 is connected via a small diameter plastic injection tube 126 and a small diameter plastic tube or conduit 127 to a cytometry flow cell 130 or other analytical instrument. The annular waste trough 124 is connected to a drain tube 132, which is in turn connected via a small diameter plastic tube 128 to a waste pump and/or waste reservoir.

In this basic configuration, the fluid handling system includes an electronically controllable primary syringe pump 112 with an integral pump motor. All of the pumps disclosed in FIGS. 1 through 20 are syringe pumps, and many acceptable kinds of syringe pumps are available commercially. However, in alternate embodiments, other kinds of pumps may be used, as described below. The pump is connected to a sample probe. The pump is operable to effect one or more of the following steps: (i) transfer of a volume of a selected sample into the probe, (ii) transfer of a sample volume from the probe through the injection port and into the instrument, at one flow rate, and (iii) transfer of the sample through the instrument at a second flow rate. In the embodiment shown in FIG. 1, the primary syringe pump 112 is configured with a motor-driven syringe 111 connected to a three-port distribution valve 110. The distribution valve 110 is in turn connected to the sample probe 104, a system fluid reservoir 114 and an auxiliary reagent bottle or reservoir 116 via small diameter flexible plastic tubing, 108, 134, and 136. The small diameter flexible plastic tubing 108, 134, and 136 may be TEFLON (polytetrafluoroethylene) tubing or polyolefin tubing with inside diameters of approximately 0.030-0.040 inches, 0.040-0.060 inches, and 0.020-0.030 inches, respectively. Other kinds and sizes of tubing may also be useable. When polyolefin tubing is used, improved results have been achieved by treating the tubing with Chromic acid (Fischer Cleaning Solution (Chromic-Sulfuric Acid) Catalog No. SC88-1) to increase the wetability of the tubing, which helps maintain the integrity of the separator bubble.

In one embodiment, e.g. for use with a flow cytometer analytical instrument, the pump is operable to inject a sample into the injection port at a rate effective to move sample material at a relatively high flow rate into the instrument, and subsequently operable to move sample material through the instrument at a relatively slow rate.

As used herein, a "pump" refers to any device capable of moving a fluid or gas. Suitable pumps include pressure sources, e.g. syringe pumps, compressed air sources, vacuum sources, pneumatic pumps, diaphragm pumps, peristaltic pumps, or connections to external sources of pressure. It is also contemplated that a relatively small pump may be used, including, e.g. an electrostatically actuated meso-pump. On such meso-pump is described in, e.g., U.S. Pat. No. 5,836,750, which is incorporated herein by reference. Accordingly, the pump may include hardware such as valves, manifolds, tubing and the like. The pump also may include controllers such as any suitable microprocessor-based programmable logic controller, personal computer controller, or the like for process control. A suitable controller includes features such as programmability, reliability, flexibility and/or durability. The suitable controller may include various input/output ports used to provide connections to open and close valves, and/or regulate and meter fluids, among other features. The controller also may include sufficient memory to store process recipes for desired applications.

An exemplary pump for use in the present invention is Cavro Instruments Corp. model XP3000 with a 500 microliter syringe.

Preferably, tubing 108 will have a volume equal to or greater than the volume of the sample well 102 so that the sample is not drawn into the syringe at any time during the operation of the system. Introduction of sample material into the syringe could contribute to sample-to-sample cross contamination. The distribution valve 110 is selectively controllable to connect the primary syringe pump 112 alternately to the sample probe 104, a system fluid reservoir 114 and an auxiliary reagent bottle or reservoir 116. Optionally, the system fluid reservoir 114 may be pressurized, for example with compressed air from a pressure source 118. In alternate embodiments, pressure source 118 may be omitted. The fluid in the system fluid reservoir 114 can be varied as necessary for particular analysis purposes. For example, the system fluid may be a sheath fluid when the fluid control system is used for flow cytometry.

One advantage of the embodiments of the invention disclosed herein is that the sample volume that may be analyzed may vary from a very small sample to a very large sample by simply varying the length of tubing 108. The ability to analyze large volume sizes is helpful for certain kinds of rare event analyses. Even if tubing 108 is not altered, the sample size can be easily varied by aspirating less than the full volume of tubing 108.

In standard operating mode, the fluid handling system in FIG. 1 operates generally as follows:

(1) System fluid is drawn into the primary syringe pump 112 from the system fluid reservoir 114.

(2) The distribution valve 110 is activated so that the primary syringe pump 112 communicates with the sample probe 104.

(3) Typically, the primary syringe pump 112 aspirates a small amount of air into the tip of the tubular member 92 of the sample probe 104 to form a separator bubble, however, the generation of a separator bubble may not be necessary for some analytical processes.

(4) With the sample probe 104 in the up position, the fluid handling system moves the well plate 100 along the X and Y axes until the selected sample well 102 is positioned below the sample probe 104, then the probe arm 106 is lowered to move the sample probe 104 into the sampling position (104B) with the tip of the probe immersed within the sample in the selected sample well 102. In alternate embodiments the probe arm 106 may be moved instead of or in addition to the movement of the well plate 100.

(5) Optionally, the sample may be mixed by the probe by the following process: the primary syringe pump 112 sucks a small first volume of sample, then alternately suck and spit a second larger volume of sample. The first volume of sample is not expelled and is used to prevent the separator bubble from being ejected from the probe. Alternatively, the process may be performed as follows: the primary syringe pump 112 sucks a first volume of sample, then the primary syringe pump 112 is reciprocated to alternately spit and suck a second slightly smaller volume of sample. If samples do not require mixing, or are pre-mixed, this step may be skipped.

(6) A sample aliquot is aspirated into the sample probe 104 (the bubble separates the sample from the system fluid).

(7) the probe arm 106 is raised to lift the sample probe 104 out of the sample well 102, the probe arm 106 is moved horizontally until it is over the injection port 120, then the probe arm 106 is lowered to move the sample probe 104 into the sample injecting position (104A) with the tubular member 92 sealingly engaging the tubing 126 connected to the central bore 122 of the injection port 120.

(8) Optionally, an additional air bubble may be aspirated into the tip of the sample probe 104 before the sample probe 104 is lowered into injection port 120 to facilitate wash-in of the sample.

(9) The primary syringe pump 112 preferably boosts the sample at a high flow rate relative to the optimal analyzing flow rate to rapidly prime the conduit 127 through the analytical instrument 130.

(10) The primary syringe pump 112 speed is reduced to the analysis rate, and sample analysis can proceed promptly at the optimal flow rate.

(11) After a suitable quantity of sample is analyzed, the remainder of the sample along with the separator bubble may be purged at high flow rate through the conduit 127 and flow cell 130 to facilitate rapid wash-out.

(12) The sample probe 104 is disengaged from the injection tubing 126, and raised into the conical portion 123 of the injection port 120.

(13) An additional volume of the system fluid is expelled by the syringe pump 112, which thoroughly washes out the sample residue from the tube 108, the sample probe 104, and also cleans a portion of the sample probe 104 exterior by flushing into the conical portion 123 of the injection port 120.

(14) Overflow of system fluid from the conical portion 123 of the injection port 120 is received in the waste trough 124 of the injection port 120, and is conveyed to waste through waste tube 128.

(15) The sample probe 104 is fully raised to proceed to the next sample well 102, and the sequence is repeated.

Boosting the sample into the analytical instrument by advancing the primary syringe pump 112 rapidly to move the sample quickly through the injection tubing 126 and the conduit 127 to the flow cell 130, then slowing the primary syringe pump 112 to a data acquisition rate suitable for gathering measurement data on the sample with the flow cell 130 increases the overall throughput of the fluid handling system and analytical instrument without compromising the accuracy of the analytical instrument. In standard throughput mode, exemplary prototype devices of the fluid handling system can prepare and analyze samples at a rate of approximately 6.6 per minute. Further optimization of the process discussed above may result in further increases in speed. Carryover performance tested on Becton Dickinson Model FACSC an flow cytometer, according to an exemplary embodiment of the invention, resulted in less than 0.05% carryover using 2.49 diameter micron nile red beads, and a stained, lysed human lymphocyte preparation as the sample.

In one variation of this method, an auxiliary reagent may be introduced and mixed with the sample, as follows:

(1) Auxiliary reagent is drawn into the syringe pump 112 from the auxiliary reagent supply container 116.

(2) The sample probe 104 tip is positioned above the injection port/wash station 120, and the reagent is primed through the pumping system.

(3) Overflow of auxiliary reagent from the conical portion 123 of the injection port 120 is received in the waste trough 124 of the injection port, and is conveyed to waste.

(4) The sample probe 104 then pumps a predetermined aliquot of reagent into each well 102 as required.

(5) Mixing of reagent with the sample in the well 102 can be accomplished non-invasively by the turbulence generated from the dispensed jet of reagent.

(6) Alternatively, in addition to the reagent dispense mixing action, a separator bubble may be aspirated into the tubular member 92, and the sample probe 104 may be lowered to execute a suck/spit type of mixing, as previously described.

In addition, the fluid handling system may be used for intra-plate pipetting, as follows:

(1) The sample probe 104 is initially primed with system fluid.

(2) Optionally, a separator bubble is aspirated into the tubular member 92 of the probe 104.

(3) Reagents residing in specified wells 102 within the tray 100 may be aspirated into the sample probe 104 tip and transferred to other wells 102.

(4) The sample probe 104 may be washed in the injection port/wash station 120 as previously discussed.

(5) Reagent may be aspirated with an intervening separator bubble, dispensed, mixed with the sample, and aspirated into the sample probe 104 for subsequent analysis.

(6) The ability to analyze the sample shortly after a reagent is added allows for analysis of short-lived events such as certain types of kinetic assays to be readily performed.

Another embodiment of the invention includes a high throughput automated handling system for use with an analytical instrument for analyzing samples. The system includes a sample-holding station for holding a plurality of samples to be analyzed. An injection port adapted to be operably coupled to the analytical instrument, and through which sample material can be supplied to the instrument is also included. A selected sample may be transferred to the injection port with a sample probe that is moveable between each of a selected sample in the station and the injection port. A first pump, as described above, may be connection to the sample probe. The first pump is operable to effect the transfer of a selected volume of sample into the probe, and to eject the sample volume through the injection port, at a first flow rate. A second pump, may be adapted to be operably placed between the injection port and the instrument, operable to control the rate of movement of the sample volume through the analytical instrument, at a second flow rate.

Figure 2:
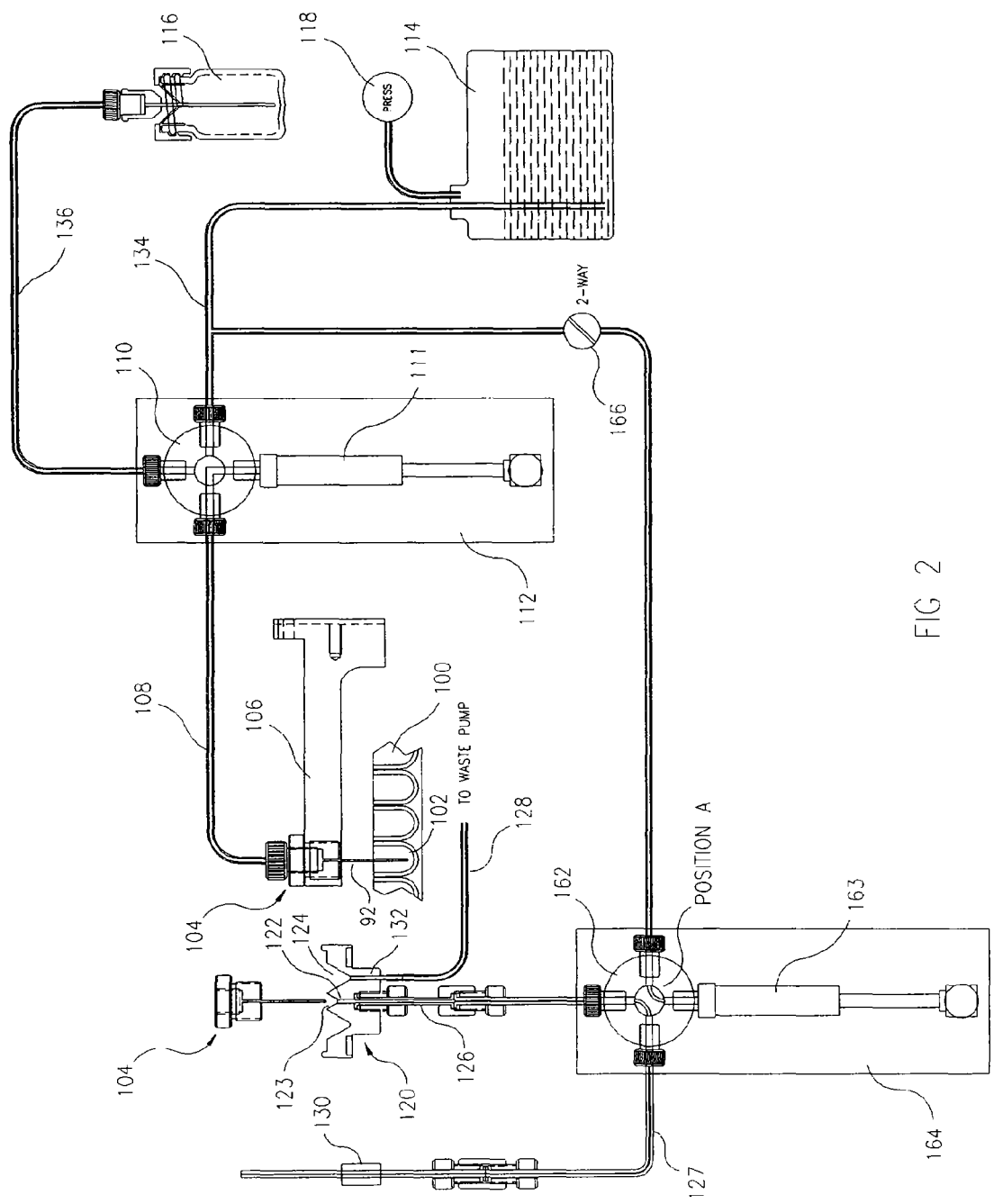
FIG. 2 is a schematic diagram of a high throughput fluid handling system configured for handling samples from a microtiter well plate shown in position A.
Figure 3:
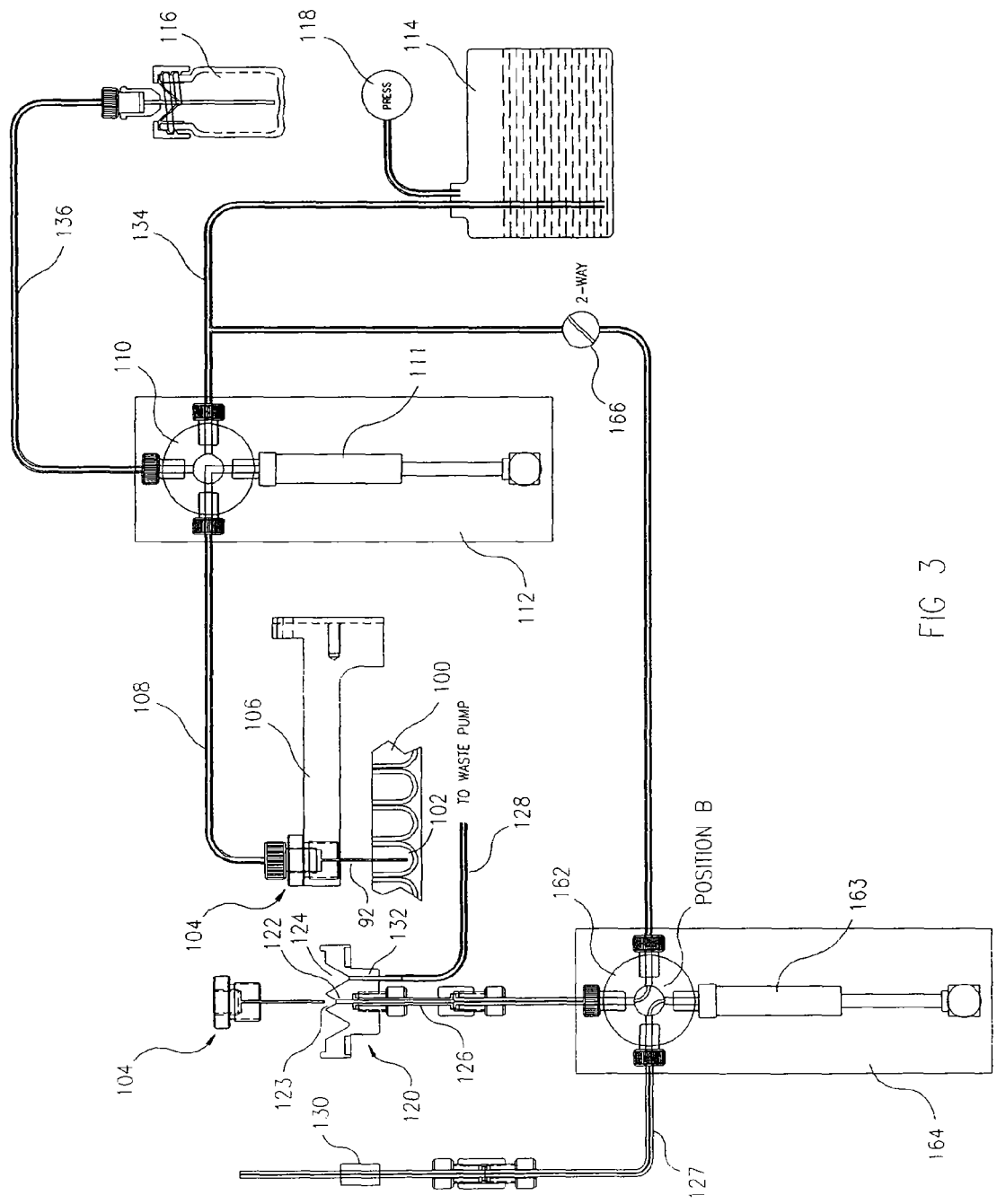
FIG. 3 is a schematic diagram of the high throughput fluid handling system of FIG. 2 shown in position B.

FIGS. 2 and 3 are schematic diagrams of a high throughput fluid handling system configured for handling samples from a microtiter well plate 100. The high throughput fluid handling system is constructed similarly to the fluid handling system of FIG. 1 with the addition of an electronically controllable secondary syringe pump 164 with an integral pump motor. The secondary syringe pump 164 is configured with a motor-driven syringe 163 connected to a four-port switching valve 162. The four-port switching valve 162 is in turn connected to the central bore 122 of the injection port/wash station 120, the conduit 127 leading to the flow cell 130, and to the system fluid reservoir 114 via two-way valve 166. FIG. 2 shows the fluid handling system with the four-port switching valve 162 in position A, connecting the central bore 122 with the conduit 127 leading to the flow cell 130 and connecting the motor-driven syringe 163 of the secondary syringe pump 164 with the system fluid reservoir 114 through the two-way valve 166. FIG. 3 shows the fluid handling system with the four-port switching valve 162 in position B, connecting the central bore 122 with the system fluid reservoir 114 through the two-way valve 166 and connecting the motor-driven syringe 163 of the secondary syringe pump 164 with the tubing 127 leading to the flow cell 130. Four-port valves may be obtained from a variety of commercial sources, e.g., the Kloehn Company (Las Vegas, Nev.).

In high throughput mode, the fluid handling system shown in FIGS. 2 and 3 may be operated as follows:

(1) System fluid is drawn into the primary syringe pump 112 from the system fluid reservoir 114.

(2) The distribution valve 110 is activated so that the primary syringe pump 112 communicates with the sample probe 104.

(3) Typically, the primary syringe pump 112 aspirates a small amount of air into the tip of the tubular member 92 of the sample probe 104 to form a separator bubble, however, the generation of a separator bubble may not be necessary for some analytical processes.

(4) With the sample probe 104 in the up position, the fluid handling system moves the well plate 100 along the X and Y axes until the selected sample well 102 is positioned below the sample probe 104, then the probe arm 106 is lowered to move the sample probe 104 into the sampling position (104) with the tip of the probe immersed within the sample in the selected sample well 102. In alternate embodiments the probe arm 106 may be moved instead of or in addition to the movement of the well plate 100.

(5) Optionally, the sample may be mixed by the probe by the following process: the primary syringe pump 112 sucks a first volume of sample, then the primary syringe pump 112 is reciprocated to alternately spit and suck a second slightly smaller volume of sample. The reason for taking a second smaller volume of sample during the mixing process is to protect the separator bubble.

(6) A sample aliquot is aspirated into the sample probe 104 (the bubble separates the sample from the system fluid).

(7) the probe arm 106 is raised to lift the sample probe 104 out of the sample well 102, the probe arm 106 is moved horizontally until it is over the injection port 120, then the probe arm 106 is lowered to move the sample probe 104 into the sample injecting position with the tubular member 92 sealingly engaging the tubing 126 connected to the central bore 122 of the injection port 120.

(8) Optionally, an additional air bubble may be aspirated into the tip of the sample probe 104 before the sample probe 104 is lowered into injection port 120 to facilitate wash-in of the sample.

(9) The primary syringe pump 112 preferably boosts the sample at a high flow rate relative to the optimal analyzing flow rate to rapidly prime the conduit 127 through the analytical instrument 130.

(10) Simultaneously with one or more steps above, while the four-port switching valve 162 is in position A, two-way valve 166 is opened and the secondary syringe pump 164 aspirates system fluid into the motor driven-syringe 163.

(11) After the sample has been boosted through the conduit 127 leading to the flow cell 130, the four-port switching valve 162 is moved to position B, and the motor-driven syringe 163 of the secondary syringe pump 164 is advanced to move the sample through the flow cell 130 at a preferred data acquisition rate, which preferred rate may include 0 velocity under some circumstances.

(12) While the four-port switching valve 162 is in position B, the probe 104 is raised into the conical portion 123 of the injection port 120, and the primary syringe pump 112 expels a volume of system fluid to remove residual sample from the conduit 108 and the probe 104 as previously described. Simultaneously, two-way valve 166 is opened to back flush system fluid from the pressurized sheath reservoir 114 through the injection tubing 126, and central bore 122 in order to clean those components of the injection port/wash station. The system fluid also flushes out the conical portion 123 of the injection port/wash station 120 and overflows into the annular waste trough 124 and is drawn out through drain tube 132 and through the plastic tube 128 by the waste pump 218.

(13) While the secondary pump 164 is flowing the sample through the analytical instrument 130 for analysis, the probe arm 106 moves the sample probe 104 to the up position and steps 1 through 9 are repeated with a sample from another sample well 102 in the well plate 100.

(14) After a suitable quantity of sample is analyzed, the remainder of the sample may be purged at high flow rate by pump 164 through the conduit 127 and analytical instrument 130 to facilitate rapid wash-out.

In alternate variations of the high throughput mode or method described above, the fluid handling system may also introduce an auxiliary reagent as described previously under the standard throughput method, and/or be used for intra-plate pipetting, as also previously described.

The high throughput method described above increases the overall throughput of the fluid handling system and the analytical instrument because the sample probe 104 and primary syringe pump 112 may be used to prepare another sample from the well plate 100 while the secondary syringe pump 164 is moving the sample through the flow cell 130. In high throughput mode, prototype fluid handling systems have processed samples at a rate of approximately 12 wells per minute, including 3.8 seconds of data acquisition time and including two suck/spit mix cycles per well. Further optimization of the high throughput method described above may result in further increases in speed.

Alternatively, the high throughput fluid handling system of FIGS. 2 and 3 may be operated in the standard operating mode by leaving the four-port switching valve 162 in position A and performing steps 1-14, as described above in connection with FIG. 1. In the standard operating mode, the fluid handling system is capable of analyzing larger volumes of samples, limited only by the volume of the tube 108 connecting the sample probe 104 to the primary syringe pump 112, whereas in the high throughput operating mode, the size of the samples to be analyzed is limited by the volume of the conduit 127 leading to the analytical instrument 130.

FIGS. 4A and 4B shows a detailed preferred timing scheme for both the standard throughput method and the high throughput methods discussed above, performed on a fluid handling system configured as shown in FIGS. 1, 2 and 3. FIG. 4A discloses a timing sequence for a standard throughput method. The left hand column of FIG. 4A lists active elements. The next column to the right lists the functions that are to be performed by each active element. The numbers increasing to the right represent a timeline, with the numbers corresponding to a time unit, wherein the time unit is preferably approximately one second. The lines identify which activity is being performed by the element and for how long. Arrows extending between events on one line and events on another line are intended to assist in the identification of times where the end of one event signals the beginning of another. For example, referencing the probe 104 in the left hand column, the probe initially begins at time 0 in the injection position. The slope up to the flush position indicates that the change in position from the inject position to the flush position occurs over a discrete period of time. The horizontal line at the top of the slope indicates that the probe 104 remains in the flush position for that time period. The probe 104, then transitions over time (indicated by the sloped line) to an up or transfer position. Now referring to the pump 111 element in the left hand column, the pump initially begins in an off condition. The pump then changes to a flush condition wherein the pump is pumping system fluid. The change in condition is relatively instantaneous, as indicated by the vertical line between the off condition and the flush condition. The first arrow extending from the probe line where the probe line has reached the flush position to the pump where the pump line reached the flush condition indicates that the occurrence of the first event signals the beginning of the second.

The process of obtaining a sample corresponding roughly to the method steps 1 through 8 of the standard throughput method discussed previously starts at 0 and progresses through approximately 4.5. The analysis steps corresponding roughly to steps 9 through 15 starts approximately at time 4.5 and extends through time 9, as indicated on the graph at the top of the figure, showing the event rate with reference to the timing of the method steps described above. As shown in the figure, the event rate rises rapidly following the boost step at approximately 4.5, drops and remains steady through approximately 8.5, and rises and falls rapidly during the purge step. The cycle could then be repeated as frequently as necessary. The dotted lines from time 9 through time 11.5 disclose a final wash cycle that may be performed by the fluid control device after the last sample has been processed.

FIG. 4B, discloses a preferred timing sequence for a high throughput method. The chart shown in this figure may be understood by reference to the explanation given for FIG. 4A above, however, the method steps are somewhat different. Specifically, the process of obtaining a sample corresponding roughly to the method steps 1 through 9 of the high throughput method discussed previously starts at time 0 and progresses through approximately time 5. The process of obtaining a sample is then repeated, while simultaneously the process of analyzing the sample, corresponding roughly to steps 10 through 14 of the high throughput method discussed above, begins at approximately time 5 and runs through time 10. The analysis may be understood by reference to the top part of the graph showing the event rate with respect to the timing of the method steps described above. The simultaneous method steps seen between time 5 and time 10 may be repeated as necessary. The method steps charted after time 10 disclose a final wash cycle that may be performed by the fluid control device after the last sample has been processed.

Figure 5:
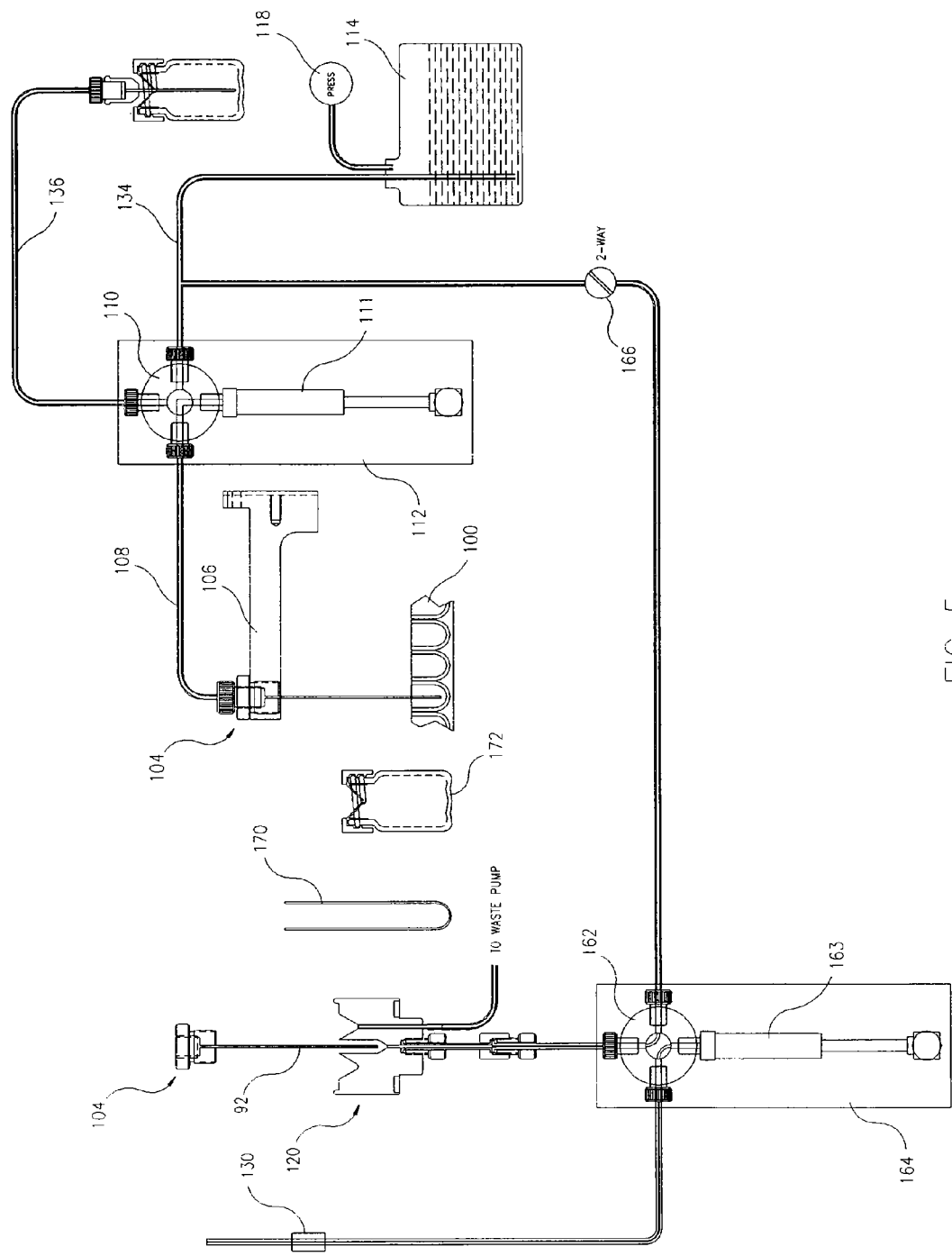
FIG. 5 is a schematic diagram of a high throughput fluid handling system configured for alternately handling samples from a microtiter well plate, a tube carousel or tube array and/or an auxiliary reagent source.

FIG. 5 is a schematic diagram of a high throughput fluid handling system configured for alternately handling samples from a microtiter well plate 100, a tube carousel or tube array 170 and/or an auxiliary reagent source 172. The fluid handling system is similar to the high throughput fluid handling system of FIGS. 2 and 3, except that the probe arm 106 and sample probe 104 are configured with additional positions for programmably gathering samples and/or reagents and diluents from one or more of the microtiter well plate 100, tube carousel or tube array 170 and/or an auxiliary reagent source 172. In this embodiment, the length selected for tubular member 92 should be sufficient for taking samples from the tube carousel or tube array 170 and the auxiliary reagent source 172, which typically requires longer reach than that required to access the wells 102 of plate 100. The central conical portion 123 has extended vertical walls to allow washing a greater immersion length of the tubular member 92.

Figure 6:
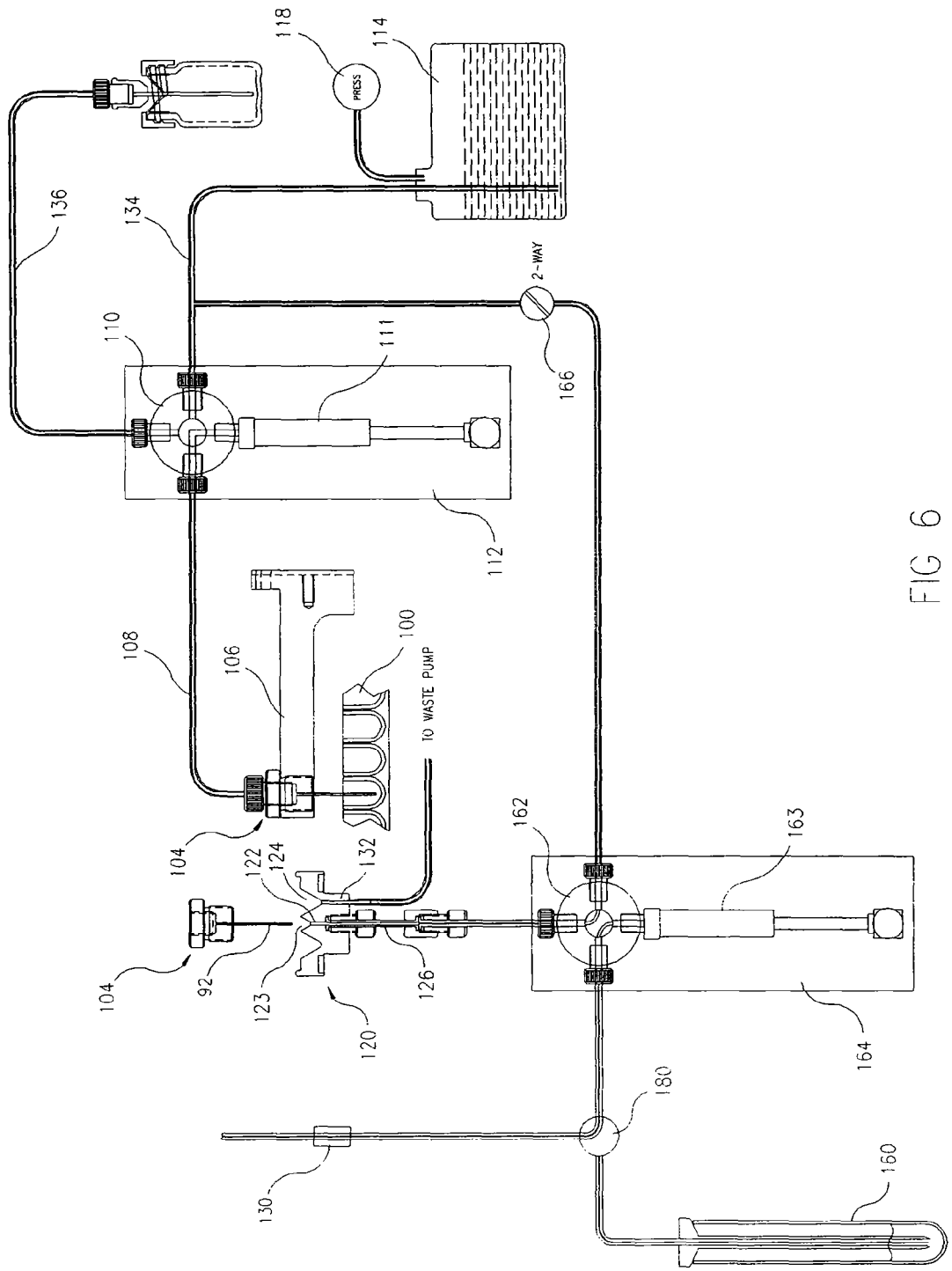
FIG. 6 is a schematic diagram of a high throughput fluid handling system with a three-way selector valve configured for alternately handling samples from a microtiter well plate, a single test tube or a tube carousel or tube array.

FIG. 6 is a schematic diagram of a high throughput fluid handling system configured for alternately handling samples from a microtiter well plate, a single test tube or a tube carousel or tube array 170. The fluid handling system is similar to the high throughput fluid handling system of FIGS. 2 and 3 with the addition of a three-way selector valve 180 that allows quick changeover for alternately handling samples from the microtiter well plate 100 and the test tube 160 or a tube carousel or tube array. The sample from the test tube 160 may be driven through the analytical device 130 by pressurized air supplied in the head space above the sample. Alternatively, the sample may be aspirated through the analytical device 130 by applying a vacuum downstream of the analytical device 130. Alternatively, it is also possible to switch valve 180 to allow syringe pump 164 to pump the sample through analytical device 130.

Figure 7:
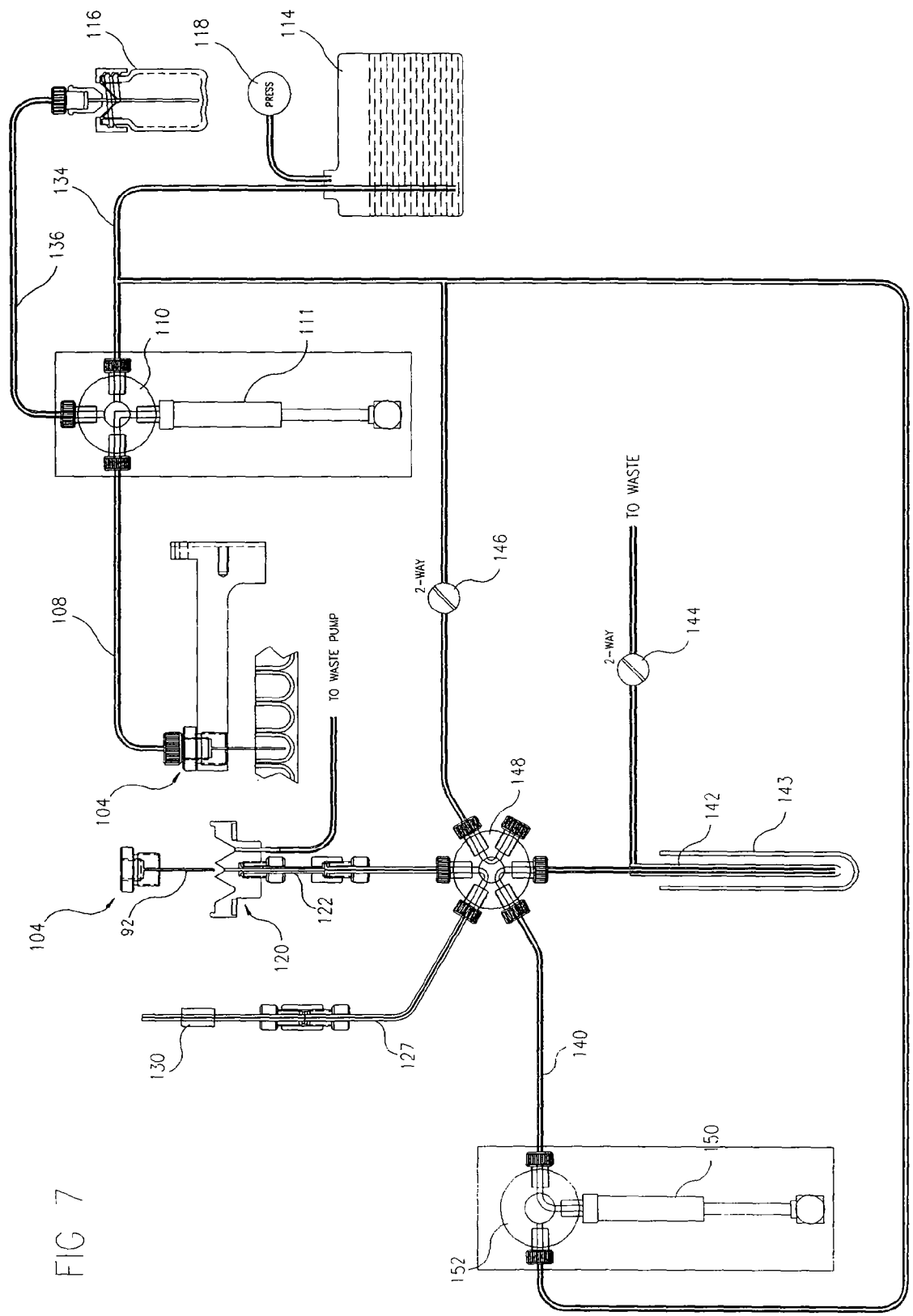
FIG. 7 is a schematic diagram of a high throughput fluid handling system configured with a sample storage loop.

FIG. 7 is a schematic diagram of a fluid handling system similar to that shown in FIGS. 2 and 3, but configured with a droplet containment probe 142 and sample storage loop 140 for handling fluid samples from a test tube 143. A six-port selector valve 148 is configured to allow a sample from a test tube 143 to be pumped through the analytical instrument 130 for analysis. A two-way valve 146 selectively connects the system fluid reservoir 114 to the selector valve 148 for back flushing the sample flow path to the injection port 120. Another two-way valve 144 selectively connects the drop containment probe 142 to a waste pump or reservoir 218. A second end of the sample storage loop 140 is selectively connected to a secondary syringe pump 150 with integral 3-way valve 152. Valve 152 selectively connects the secondary syringe pump 150 to the sample storage loop 140 or the sheath supply 114. This configuration allows samples not residing in a well plate to be introduced into the fluid handling system through the separate probe 142. The sample is aspirated from the test tube 143 via the droplet containment probe 142 into the sample storage loop 140 by the secondary syringe pump 150. The selector valve 148 is then switched so that sample is pumped through the analytical instrument 130 with system fluid from the secondary syringe pump 150. The sample storage loop 140 and droplet containment probe 142 may be cleaned after the analysis by flowing sheath solution back through the probe 142, when the selector valve 148 is switched back to the position shown in FIG. 7. The back flow is conveyed to waste via suction through the annular space within the droplet containment probe 142 and through two-way valve 144 to waste 218.

Alternatively, for operation with a microtiter well plate 100, the fluid handling system of FIG. 7 may be operated in the standard operating mode or the high throughput mode, as described above in connection with FIGS. 1 through 4.

FIG. 7A is a schematic diagram of a high throughput fluid handling system configured similarly to FIG. 7, but further including an additional fluid conduit controlled by valve 146A that may be linked through valve 148 to back flush the sample tube 142.

Figure 8:
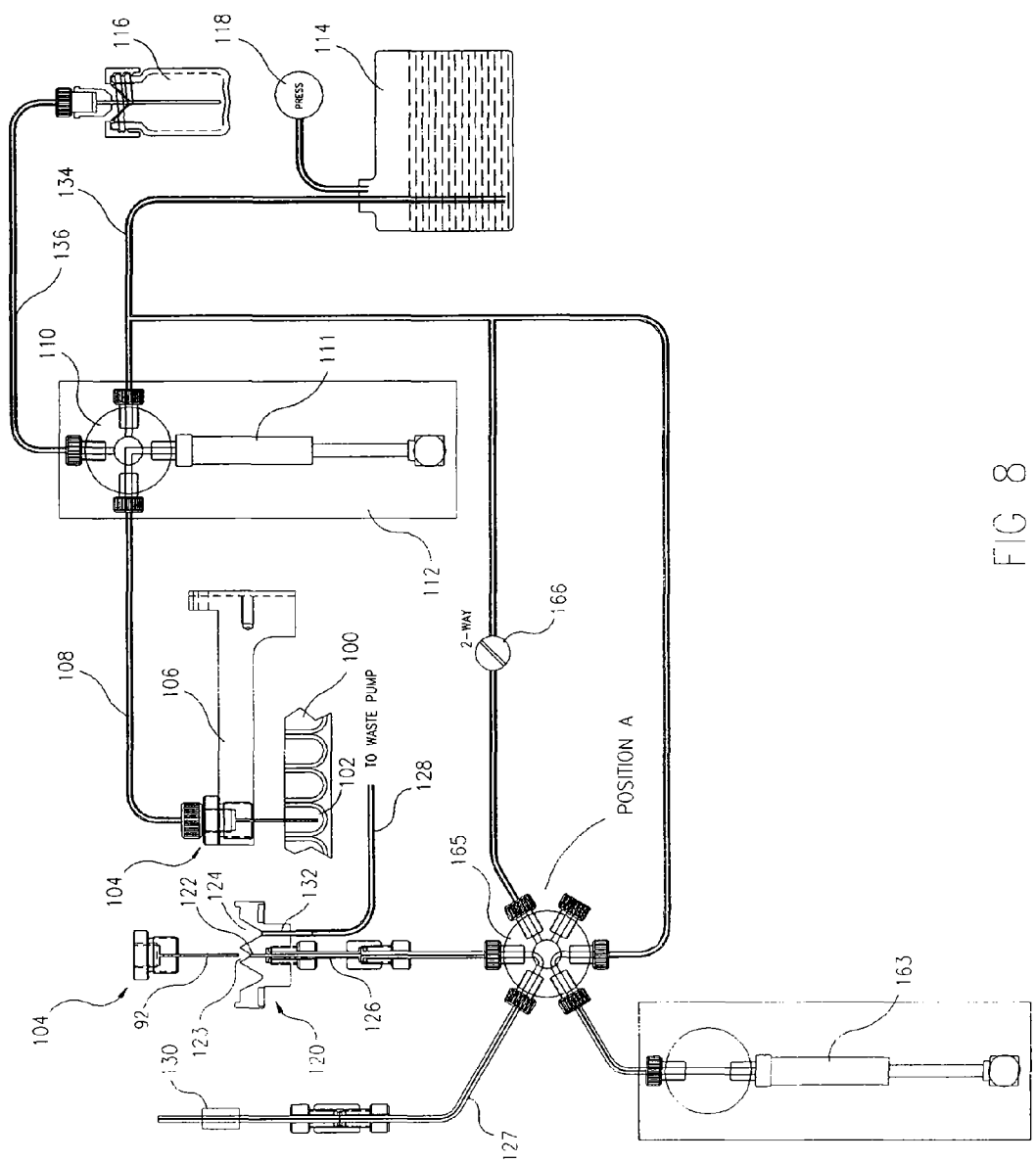
FIG. 8 is a schematic diagram of a high throughput fluid handling system configured with a six-port, two-position valve shown in position A.
Figure 9:
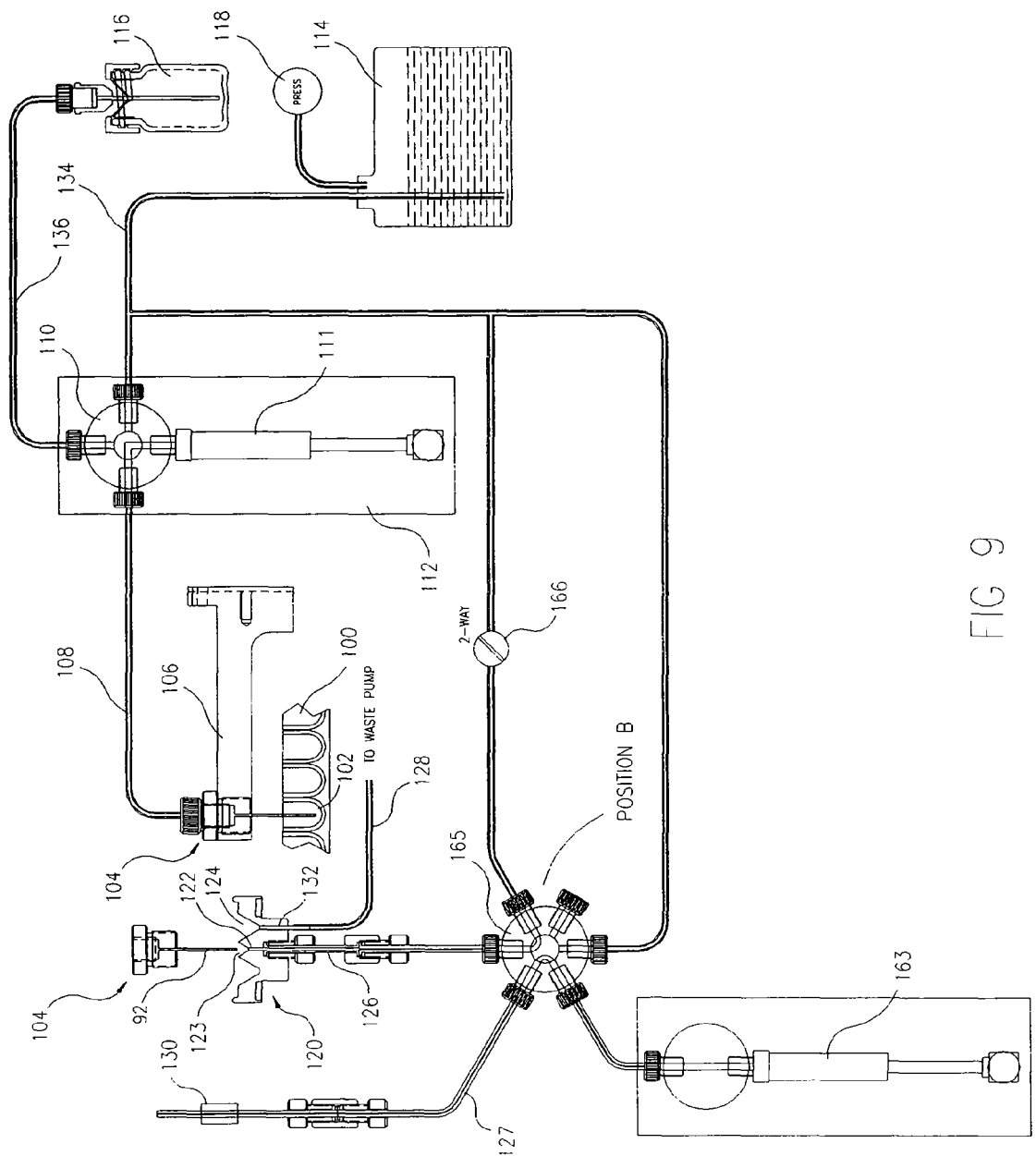
FIG. 9 is a schematic diagram of the high throughput fluid handling system of FIG. 8—shown in position B.

FIG. 8 is a schematic diagram of a high throughput fluid handling system configured with a six-port, two-position valve 165, shown in position A. FIG. 9 is a schematic diagram of the high throughput fluid handling system of FIG. 8 shown in position B. This embodiment of the fluid handling system operates similarly to the embodiment described in FIGS. 2 and 3. With the six-port, two-position valve 165 in position A, the primary syringe pump 112 boosts the sample into the flow cell 130 at a high flow rate. Then, the six-port, two-position valve 165 is switched to position B and the secondary syringe pump 164 advances the sample through the analytical instrument 130 at a lower flow rate for data acquisition. This frees up the sample probe 104 and the primary syringe pump 112 to repeat the cycle of washing and obtaining another sample while the first sample is analyzed. An exemplary six-port valve is the Valco Instruments Co, Inc. (Houston, Tex.) Model designation C2 or C22 six port valve with a microelectric two position actuator.

Figure 11:
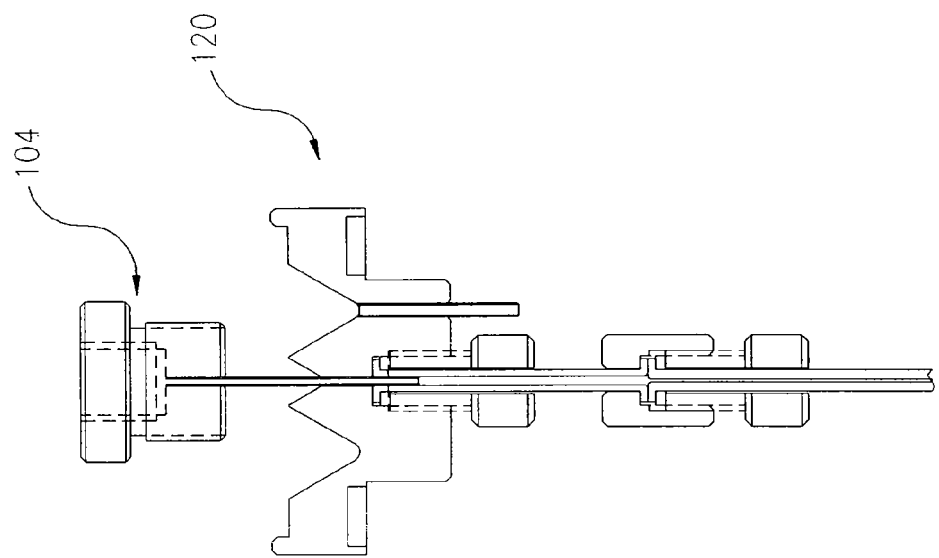
FIG. 11 is a cross section showing the sample probe inserted into the injection port of the fluid handling system.
Figure 10:
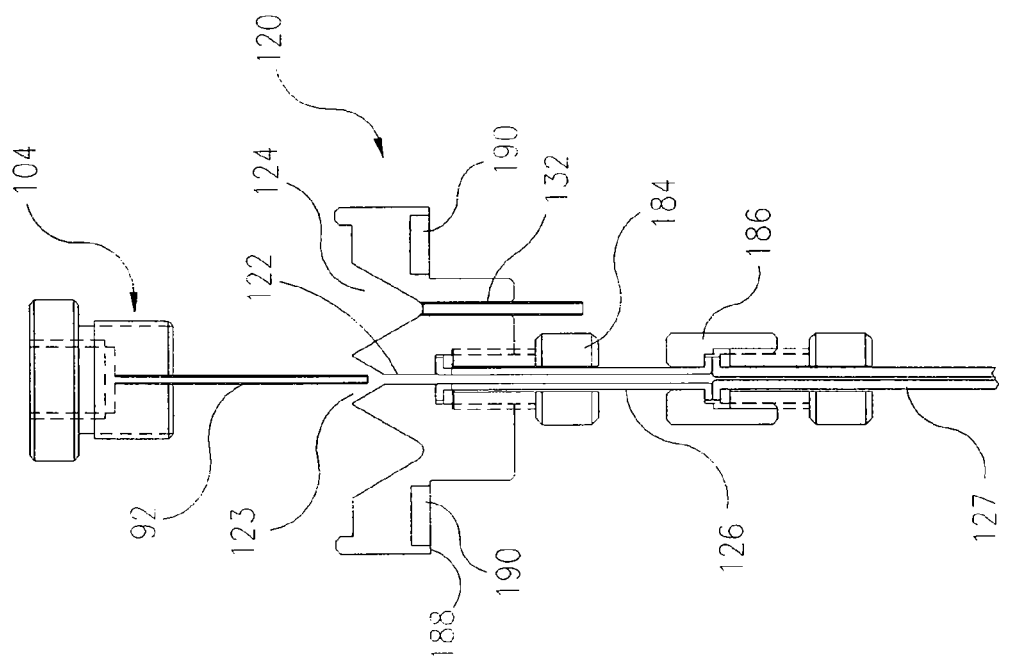
FIG. 10 is a cross section showing the sample probe positioned above the injection port of the fluid handling system.

FIGS. 10 and 11 illustrate a preferred embodiment of a sample probe 104 and an injection port/wash station 120 for use with the fluid handling system of the present invention. FIG. 10 is a cross section showing the sample probe 104 positioned above the injection port/wash station 120 of the fluid handling system in the flush or rinse position. FIG. 11 is a cross section showing the sample probe 104 in the injecting position with the sample probe 104 sealingly engaging the injection tubing 126 connected to the central bore 122 of the injection port/wash station 120. Typically, the tubular member 92 is made of 316 stainless steel hypodermic tubing with a blunt end. In one preferred embodiment, the tubular member 92 has an outside diameter of approximately 0.028 inches. The length of the tubular member 92 should be sufficient to reach the bottom of the sample wells 102 in the well plate 100, or alternatively, the test tubes or other containers that may be used.

Referring to FIG. 10, the injection port/wash station 120 has a central conical portion 123 connected to a central bore 122, which is surrounded by an annular waste trough 124. In this preferred embodiment, the central bore 122 is connected via an injection tube 126 to a small diameter plastic tube or conduit 127 leading to an analytical instrument identified as analytical instrument 130 or to the valve of a second pump 164 in high throughput embodiments. The injection tube 126 is preferably a TEFLON (polytetrafluoroethylene) or polyolefin tube with an internal diameter of approximately 0.025 inches to create an interference fit and a seal with the sample probe 104 when it is in the injecting position, as shown in FIG. 9. The injection tube 126 is preferably joined to the injection port/wash station 120 and the plastic tube 127 by a pair of flare-type compression fittings 184, 186 to allow quick replacement of the injection tube 126. The small diameter plastic tube 127 leading to the analytical instrument 130 is preferably a TEFLON (polytetrafluoroethylene) or polyolefin tube with an internal diameter of approximately 0.010 inches.

The annular waste trough 124 is connected to a drain tube 132, which may comprise stainless steel, and which is in turn connected via a small diameter plastic tube 128 to a waste pump and/or reservoir 218. The injection port/wash station 120 may be machined or injection molded out of plastic, such as acrylic or polycarbonate, however, other materials may be useable. The injection port/wash station 120 is circular from a top view in one preferred embodiment, which simplifies machining of the part and/or mold. However, other shapes may also be used. The injection port/wash station 120 has a shoulder 188 in which are embedded six small magnets 190. The magnets 190 provide easy attachment and precise registration of the injection port/wash station 120 with the injection port holder 200 of the fluid handling system shown in FIG. 14, which has six corresponding magnets 202 of opposite polarity. In alternate embodiments, a different number or configuration of magnets 190, 202 may be used. To remove the injection port/wash station 120 from the injection port holder 200, the injection port/wash station 120 is rotated slightly to disengage the magnets 190, 202 from one another, then the injection port/wash station 120 can easily be lifted off of the injection port holder 200. An exemplary magnet for use in the present invention is a {fraction (3/16)} diameter by {fraction (1/16)} thick Neodymium Iron Boron magnet.

FIG. 12 is a cross section of an alternate embodiment of the injection port/wash station 120. In this embodiment, a tubular member 92 with an exterior diameter of approximately 0.028 inches is inserted into the central bore 122 and the plastic tube 126 leading to the analytical instrument 130. The plastic tube 126 includes an initial internal diameter approximately 0.025 inches to accept the tubular member 92, then reduces to a smaller diameter of approximately 0.010 inches. The injection tube 126 is preferably joined to the injection port/wash station by a flare-type compression fitting 184 to allow quick replacement of the injection tube 126. There are preferably six magnets 190 embedded in the shoulder 188 of the injection port/wash station 120 and six corresponding magnets 202 of opposite polarity in the injection port holder 200, as shown in FIG. 14.

FIG. 13 is a cross section of a second alternate embodiment of an injection port/wash station assembly 120. In this embodiment, the injection port 194 and the wash station 196 are separately molded or machine parts that are then assembled together. Preferably, at least the injection port 194 is made as a low-cost, disposable injection molded part. There are preferably six magnets 190 embedded in the shoulder 188 of the injection port/wash station 120 and six corresponding magnets 202 of opposite polarity in the injection port holder 200.

FIG. 14 is a top view of the injection port holder 200 of the fluid handling system. FIG. 15 is a side view of the injection port holder 200. FIG. 16 is a cross section of the injection port holder 200 taken along line A-A in FIG. 12. The injection port holder 200 is generally rectangular in shape with a raised wall 208 around the periphery to capture any inadvertent spillage of sample fluid, system fluid or other reagents. A circular through hole 204 is sized to accommodate the injection port/wash station 120. In one embodiment, the circular through hole 204 is somewhat larger than the portion of the injection port/wash station 120 that is accepted within the through hole 204. This allows the injection port/wash station 120 to shift if contacted off center by the tubular member 92, allowing self-centering of the injection port/wash station 120. Optionally, a slot 206 extends laterally from the circular through hole 204 for additional drainage. Six magnets 202 (five magnets 202 if the optional slot 206 is present) of opposite polarity to the magnets 190 in the injection port/wash station 120, as shown in FIGS. 10 and 12, are arranged around the periphery of the injection port holder 200.

FIGS. 17-20 show the physical layout of one preferred embodiment of the fluid handling system of the invention. Many other arrangements of the fluid handling system are also possible, and the embodiments seen in FIGS. 17-20 are provided only as examples of current embodiments. FIG. 17 is a top view of the fluid handling system and FIG. 18 is an end view of the lower portion of the fluid handling system. Most of the major mechanical and electrical components of the fluid handling system are enclosed within a housing 210, including a power supply, a programmable electronic motion controller 214, and other mechanical and electromechanical components. This arrangement provides a very compact fluid handling system with a small footprint of only 9.times.12 inches in the embodiment shown. The waste pump may be, for example, a KNF Neuberger Model NF30 pump with integral motor. The programmable electronic motion controller 214 may be a Logosol 4-axis DC motor driver/controller board with integral amplifiers, with a 24 VDC power input and an RS-232 communication port for connecting to a host computer. Components usable in place of those listed are commercially available and easily found.

The three-port distribution valve 110 and the primary syringe pump 112 (and also the second valve 162 and pump 164 (FIG. 2 or 3), if used) which may be a Cavro XP3000 syringe pump with 24,000 micro steps/full stroke, with a 24 VDC power input and an RS-232 communication port for connecting to the host computer, is mounted in the interior of the housing 210, but with portions visible to provide visual confirmation of the operation of the fluid handling system, and to ease syringe and valve replacement. Other kinds and makes of pumps and valves may be useable.

Figure 19:
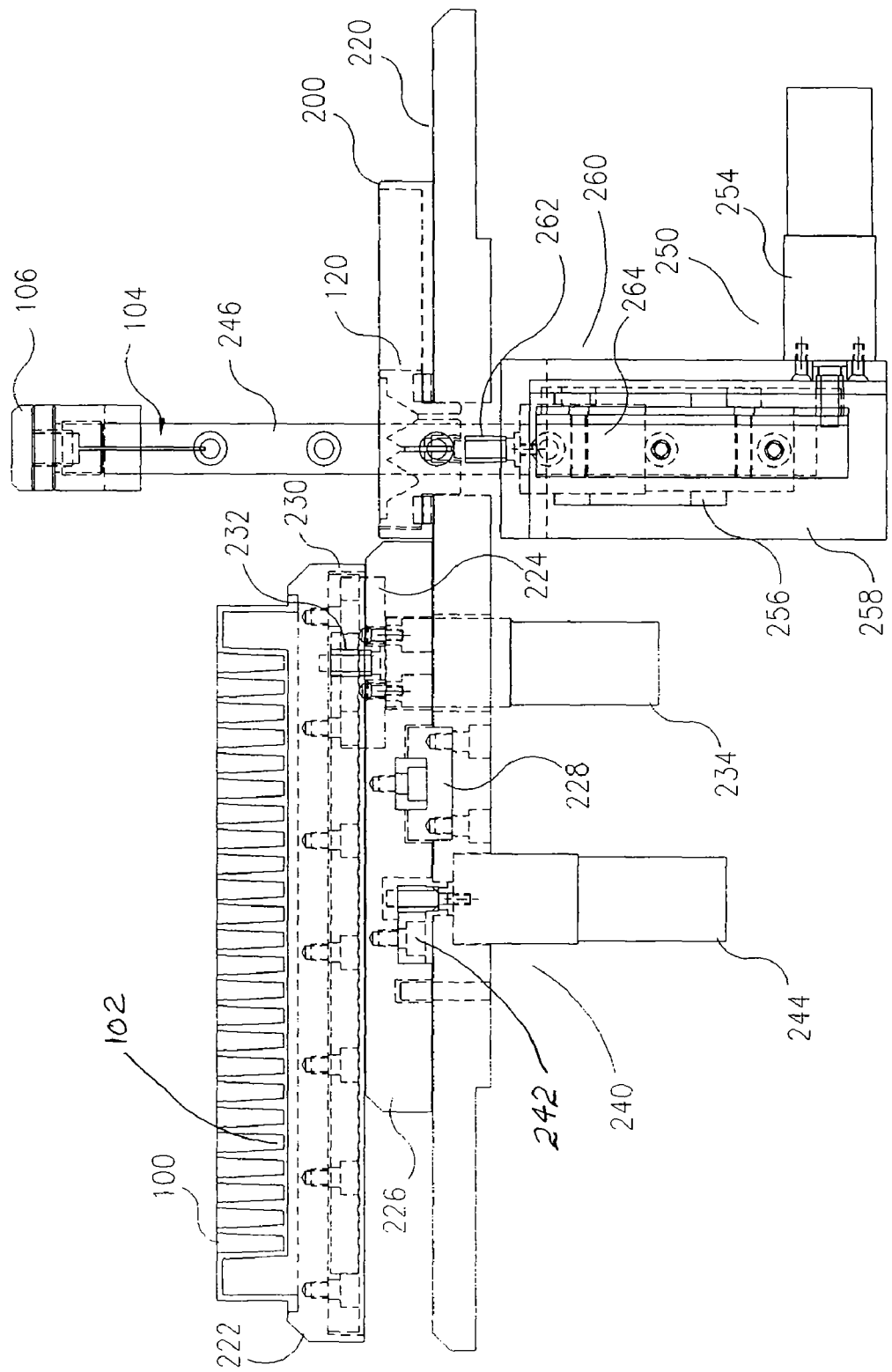
FIG. 19 is a side view of the upper portion of the fluid handling system.
Figure 20:
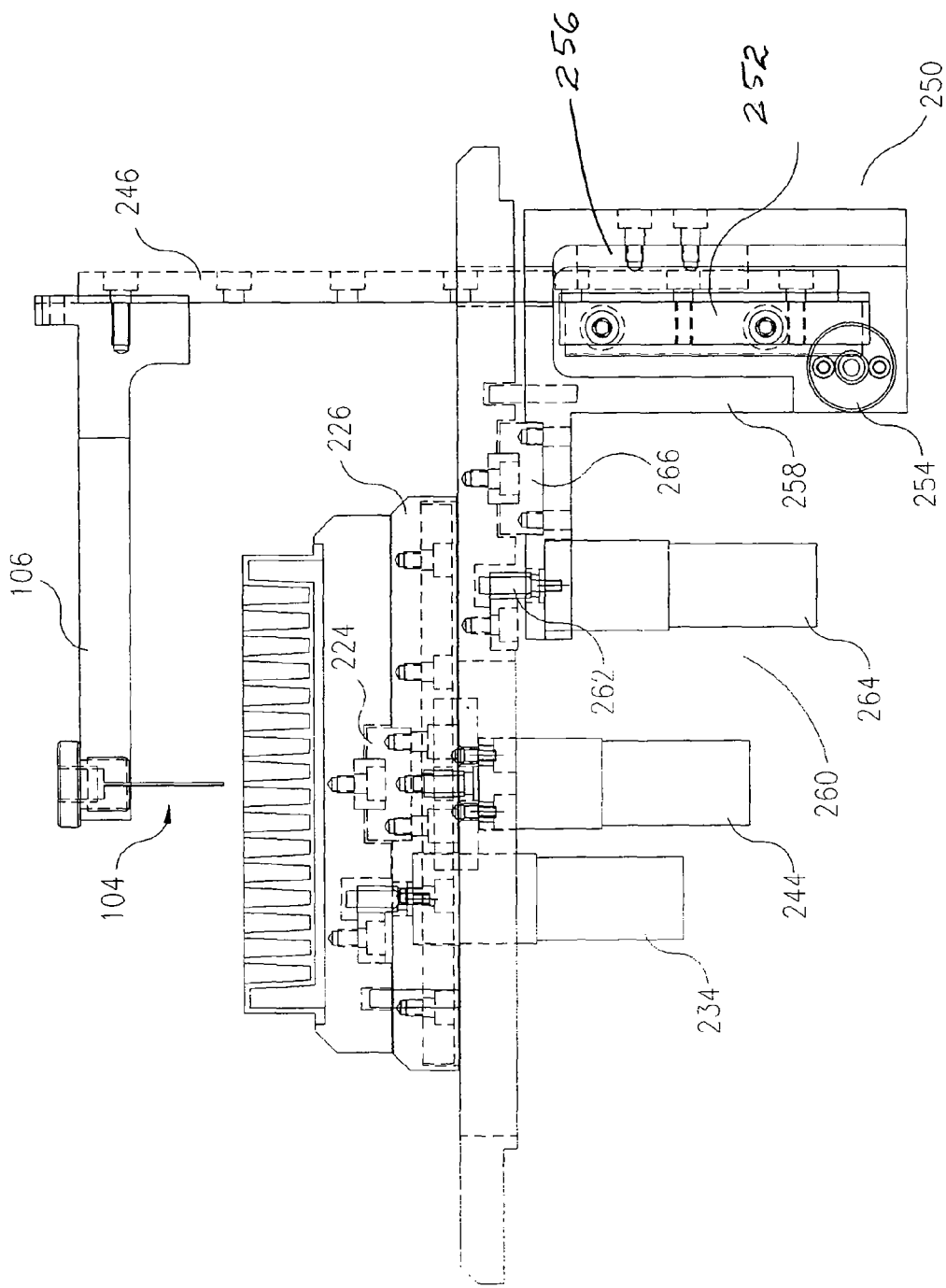
FIG. 20 is an end view of the upper portion of the fluid handling system.

FIG. 19 is a side view of the upper portion of the fluid handling system and FIG. 20 is an end view of the upper portion of the fluid handling system. The injection port holder 200 (FIG. 17), into which is inserted the injection port/wash station 120, is mounted directly on the base plate 220 of the housing 210 (FIG. 18). Extending above the base plate 220 of the housing 210 are an X-stage 222, to which the well plate 100 is removably mounted, and the probe arm 106 and the sample probe 104. The X-stage 222 is slidably mounted by way of a first linear bearing 224 oriented along the Y-axis to a Y-stage 226. The Y-stage 226 is in turn slidably mounted by way of a second linear bearing 228 oriented along the X-axis to the base plate 220 of the housing 210. A first linear actuator 230, which in this preferred embodiment includes a first rack-and-pinion 232 driven by a first gearmotor 234, provides the motion of the X-stage 222 with respect to the Y-stage 226 along the Y-axis. A second linear actuator 240, which in this preferred embodiment includes a second rack-and-pinion 242 driven by a second gearmotor 244, provides the motion of the Y-stage 226, and hence the X-stage 222, with respect to the base plate 220 of the housing 210 along the X-axis. The gearmotors 234, 244 extend below the base plate 220 into the housing 210 to keep the configuration compact. The first linear actuator 230 and the second linear actuator 240 allow the fluid handling system to selectively address any of the sample wells 102 in the well plate 100 by moving the X-stage 222 and Y-stage 226 to align the selected sample well 102 with the sampling position of the sample probe 104. In alternate embodiments, other types of linear actuators may be used in place of this rack-and-pinion/gearmotor arrangement.

The probe arm 106 and the sample probe 104 are mounted on a vertical rail 246, which is slidably mounted by way of a vertically-oriented third linear bearing 256 to a carriage 258. The carriage 258 is in turn slidably mounted by way of a horizontally-oriented fourth linear bearing 266 to the base plate 220 of the housing 210 (FIG. 18). Vertical motion of the rail 246, and hence the probe arm 106 and the sample probe 104, with respect to the carriage 258 is provided by a third linear actuator 250, which in this preferred embodiment includes a third rack-and-pinion 252 driven by a third gearmotor 254. Horizontal motion of the carriage 258, and hence the probe arm 106 and the sample probe 104, with respect to the base plate 220 of the housing 210 is provided by a fourth linear actuator 260, which in this preferred embodiment includes a fourth rack-and-pinion 262 driven by a fourth gearmotor 264. The third linear actuator 250 and the fourth linear actuator 260 allow the fluid handling system to selectively move the sample probe 104 to each of the sampling position, the up position, the rinsing position, mixing position, and the injecting position at appropriate times during the mixing/sampling/injecting/washing sequence of the methods described above. In alternate embodiments, other types of linear actuators may be used in place of this rack-and-pinion/gearmotor arrangement.

Preferably, the electrical and mechanical components of the fluid handling system are standardized to provide cost savings through bulk purchasing of components and to simplify assembly and repair of the system. Each of the linear bearings 224, 228, 256, 266, may be, for example, a THK linear recirculating ball slide model RSR9ZMUUC1. Each of the gearmotors 234, 244, 254, 264, may be a Maxon A-max 16 mm, 2 watt ironless core, precious metal brush DC motor with a 19/1 planetary gear head and a 64 quadrature count per revolution integral encoder. Each rack-and-pinion 232, 242, 252, 262 may be a steel rack 0.4 module, 5 mm face width, with a steel pinion having 12 teeth, a 5 mm face width and a 3 mm bore.

As can be seen from the figures and the preceding description, the advantages of the described embodiments of the fluid handling system may include but are not limited to: the ability to prepare samples for chemical and/or biological analysis and to introduce the samples into an analytical instrument, configurability to handle samples and reagents from microtiter well plate, test tube or reagent bottle, and/or tube carousel formats, rapid changeover between different sample and reagent formats, the ability to quickly and efficiently handle samples according to an automated program, easy configurability to provide a standard throughput mode and a high throughput mode, accurate intra-plate reagent pipetting and bulk reagent addition that allows flexible automated onboard sample preparation, low carryover between samples to avoid sample contamination, precision and accuracy obtained in some embodiments from syringe pump-controlled delivery of reagents and samples, good sample conservation and utilization (less than 10.mu.1 dead volume sample per well), adaptable to interface with an automatic tray loader, configurable with a bar-code reader for identification and positioning of well plates, and a compact size. User selectable parameters include: standard and high throughput modes, suck/spit mixing with selectable speed, acquisition volume, number of events, and number of mix cycles, selectable acquisition volume, selectable addition of auxiliary reagents, selectable sample flow rates, and the ability to address many kinds of plate and well formats.

While the present invention has been described herein with respect to the exemplary embodiments and the best mode for practicing the invention, it will be apparent to one of ordinary skill in the art that many modifications, improvements and subcombinations of the various embodiments, adaptations and variations can be made to the invention without departing from the spirit and scope thereof.

What is claimed is:

1. An analytical system comprising:
an analytical instrument having a detection zone;
a sample holding station holding a plurality of samples;
an injection port;
a system fluid reservoir containing a system fluid;
a sample probe which is movable between the samples in said sample holding station and said injection port and which transfers a selected sample from the sample holding station to the injection port;
a first pump connected to the sample probe to draw the selected sample into the probe and to eject the selected sample into the injection port;
a switching valve having a first position which connects the injection port to the detection zone to allow the first pump to deliver samples through the injection port to prime a flow path from the switching valve to the detection zone with sample;
a second pump connected to the switching valve, wherein the switching valve has a second position which disconnects the injection port from the detection zone and connects the second pump to the detection zone, the second pump being operable to advance system fluid through the flow path to displace sample in the flow path and control the volume and the rate of movement of the sample primed by the first pump through the detection zone; and
a controller which in a first mode selectively positions the switching valve in its first position and operates the first pump to deliver sample through the switching valve to prime the flow path to the detection zone and which in a second mode positions the switching valve in its second position and operates the second pump to deliver system fluid through the switching valve to advance the primed sample through the flow path to the detection zone.

2. A system as in claim 1, wherein the second position of the switching valve connects the system fluid reservoir to the injection port to backwash a flow path between the switching valve and the injection port.

3. A system as in claim 1, wherein the first position of the switching valve connects the second pump to the system fluid reservoir to receive system fluid therefrom, and wherein said received system fluid can be advanced through the flow path when the switching valve is in the second position.

4. A system as in claim 1, further comprising a distribution valve having a first position which connects the first pump to the sample probe and a second position which connects the first pump to the system fluid reservoir.

5. A system as in claim 4, wherein the system fluid reservoir is pressurized.

6. A system as in claim 1, wherein at least one of the first pump and the second pump comprises a syringe pump.

7. A system as in claim 6, wherein both the first pump and second pump comprise syringe pumps.

8. A system as in claim 1, wherein the analytical instrument comprises a flow cytometer.

9. A system as in claim 1, wherein the sample-holding station comprises a motion-controlled stage and a microtiter well plate, wherein the stage selectively positions the microtiter well plate with respect to the sample probe.

10. A system as in claim 1, wherein the injection port has a central conical portion with a central bore for receiving the sample probe and an annular waste trough surrounding the central conical portion.

11. A system as in claim 10, wherein the system further comprises an injection port holder and wherein the injection port further comprises a plurality of magnets affixed to the injection port and a plurality of opposite polarity magnets affixed to the injection port holder for attachment and registration of the injection port with respect to the injection port holder, whereby the injection port is detachable from the injection port holder by rotating the injection port to disengage the magnets from one another and lifting the injection port from the injection port holder.

12. A system as in claim 10, wherein the injection port further comprises a resilient tube in fluid communication with the central bore of the injection port, the resilient tube having an internal diameter sized to create an interference fit when the sample probe is inserted into the resilient tube.

13. A system as in claim 1, further including a chromic acid treated polyolefin tube between the sample probe and the first pump.

14. A system as in claim 1, wherein the switching valve in the second position during the second mode directs system fluid through the injection port to backwash a flow path between the switching valve and the injection port.

* * * * *